United States Patent
Noel

(10) Patent No.: US 11,872,259 B2
(45) Date of Patent: Jan. 16, 2024

(54) PROCESSES AND SYSTEMS FOR CONVERTING CANNABINOIDS INTO CANNABINOID DERIVATIVES AND ISOLATING THE SAME

(71) Applicant: Armand J. Noel, Tempe, AZ (US)

(72) Inventor: Armand J. Noel, Tempe, AZ (US)

(73) Assignee: Super Critical IP, LLC, Phoenix, AZ (US)

( * ) Notice: Subject to any disclaimer, the term of this patent is extended or adjusted under 35 U.S.C. 154(b) by 0 days.

(21) Appl. No.: 17/813,716

(22) Filed: Jul. 20, 2022

(65) Prior Publication Data

US 2023/0032547 A1     Feb. 2, 2023

Related U.S. Application Data

(60) Provisional application No. 63/227,875, filed on Jul. 30, 2021, provisional application No. 63/227,542, filed on Jul. 30, 2021.

(51) Int. Cl.

| | | |
|---|---|---|
| *C07C 37/00* | (2006.01) | |
| *C07C 37/74* | (2006.01) | |
| *C07C 37/84* | (2006.01) | |
| *A61K 36/28* | (2006.01) | |
| *A61K 36/185* | (2006.01) | |
| *A61K 31/05* | (2006.01) | |
| *A61K 31/352* | (2006.01) | |
| *C07D 311/80* | (2006.01) | |

(52) U.S. Cl.
CPC .............. *A61K 36/28* (2013.01); *A61K 31/05* (2013.01); *A61K 31/352* (2013.01); *A61K 36/185* (2013.01); *C07C 37/003* (2013.01); *C07C 37/74* (2013.01); *C07C 37/84* (2013.01); *C07D 311/80* (2013.01); *A61K 2236/35* (2013.01); *A61K 2236/37* (2013.01); *A61K 2236/51* (2013.01); *A61K 2236/53* (2013.01); *C07B 2200/13* (2013.01); *C07C 2601/16* (2017.05)

(58) Field of Classification Search
CPC ....... C07C 37/003; C07C 37/74; C07C 37/84; C07B 2200/13; A61K 31/658
See application file for complete search history.

(56) References Cited

U.S. PATENT DOCUMENTS

| | | | | |
|---|---|---|---|---|
| 2,419,937 | A * | 5/1947 | Adams | C07D 311/80 |
| | | | | 549/390 |
| 7,399,872 | B2 * | 7/2008 | Webster | C07D 311/80 |
| | | | | 549/390 |
| 2004/0143126 | A1 | 7/2004 | Webster et al. | |

FOREIGN PATENT DOCUMENTS

WO     2016-179581     11/2016

OTHER PUBLICATIONS

Marzullo, P. et al. "Cannabidiol as the Substrate in Acid-Catalyzed Intramolecular Cyclization" pp. 2894-2901. Journal of Natural Products. vol. 83, No. 10. Sep. 2020.

* cited by examiner

*Primary Examiner* — Sikarl A Witherspoon
(74) *Attorney, Agent, or Firm* — Spencer Fane LLP

(57) ABSTRACT

Some variations provide a process of converting a cannabinoid into a purified cannabinoid derivative, comprising: providing a starting composition comprising a cannabinoid; providing a $C_9$-$C_{11}$ non-aromatic hydrocarbon solvent; introducing the starting composition and the solvent to a conversion reactor; chemically converting some, but not all, of the cannabinoid to a cannabinoid derivative, generating a reaction mixture containing unreacted cannabinoid; conveying the reaction mixture to a crystallization unit; cooling the reaction mixture to precipitate unreacted cannabinoid out of the reaction mixture, thereby generating a mother liquor containing the cannabinoid derivative; and isolating and recovering the cannabinoid derivative from the mother liquor. Systems configured to carry out the disclosed processes are also provided. This invention offers a large-scale solution to economically convert CBD to D9-THC, among many other example. The principles of the invention may be applied to the conversion of various cannabinoids and terpenes into derivative products.

94 Claims, 4 Drawing Sheets

PROCESSES AND SYSTEMS FOR CONVERTING CANNABINOIDS INTO CANNABINOID DERIVATIVES AND ISOLATING THE SAME

PRIORITY DATA

This U.S. non-provisional patent application claims priority to U.S. Provisional Patent App. No. 63/227,542, filed on Jul. 30, 2021, and to U.S. Provisional Patent App. No. 63/227,875, filed on Jul. 30, 2021, each of which is hereby incorporated by reference herein.

FIELD OF THE INVENTION

The present invention generally relates to processes and systems for converting cannabinoids into purified cannabinoid derivatives, and for converting terpenes into purified terpene derivatives.

BACKGROUND OF THE INVENTION

Compound isolation is an important process during the clean-up or production of certain compounds. Many chemical-engineering unit operations are configured for compound isolation. These processes include crystallization, distillation, chromatography, filtration, and many other. Crystallization is a proven technique to produce high-purity compound mixtures and for this reason crystallization is the foundation for many pharmaceutical processes.

Crystallization is generally the process by which a solid forms, where the atoms or molecules are highly organized into a structure known as a crystal. Some of the ways by which crystals form are precipitating from a solution, freezing, or more rarely deposition directly from a gas.

Compound crystallization via precipitation from solution is dependent on the solubility of the compound in a certain solvent over a broad temperature range. The goal is to choose a solvent for which the compound (the solute) is soluble at high temperatures, but insoluble or at least less soluble at lower temperatures. Initially, the compound is dissolved into the solvent at a high temperature. As the temperature of the solution decreases, the solute becomes oversaturated (higher than equilibrium concentration) and begins to precipitate out of the solution as a solid crystal.

Biomass extracts have been used as a source of medicine throughout history and continue to serve as the basis for many pharmaceuticals, cosmeceuticals, and nutraceuticals today. Valuable biomass extracts include, but are by no means limited to, hemp, hops, chamomile, dandelion, *echinacea*, marigold, lavender, and many other therapeutic plants and herbs.

Cannabinoids are compounds found in the *Cannabis* plant. The *Cannabis* plant has been used for both medical and recreational purposes since prehistoric times, and is finding increasing scientific interest and acceptance for applications in modern medicine. *Cannabis sativa* and *Cannabis indica* are the species most often utilized. The *Cannabis* plant contains hundreds of individual compounds, including over 100 cannabinoids. Notable cannabinoids include tetrahydrocannabinol (THC) and cannabidiol (CBD) which are commonly extracted from the *Cannabis* plant on a commercial basis. THC is believed to be involved in a plant's evolutionary adaptation, putatively against insect predation, ultraviolet light, and environmental stress.

The chemical formula for THC ($C_{21}H_{30}O_2$) includes multiple isomers. A commercially desirable isomer is (−)-trans-$\Delta^9$-tetrahydrocannabinol, which is known as the delta-9-THC isomer, $\Delta^9$-THC, or D9-THC. D9-THC, as well as other cannabinoids that contain a phenol group, possess mild antioxidant activity sufficient to protect neurons against oxidative stress, such as that produced by glutamate-induced excitotoxicity. D9-THC is the principal psychoactive constituent of the *Cannabis* plant.

D9-THC has been typically grown and extracted from marijuana. However, as consumer demand increases including for pharmaceutical uses, the production of D9-THC concentrates is proving much harder to scale than the high sales demand. D9-THC grown indoors has proven to be the highest-quality material on the market, but the cost to perform this operation has caused strain on the largest D9-THC producers in the world. In the effort to reduce cost, researchers have gone down the path of chemically converting hemp-derived CBD into D9-THC. The conversion of cannabinoids is known in the pharmaceutical industry. For example, dronabinol is a well-known pharmaceutical drug that utilizes the conversion of CBD into D9-THC.

There is a need for a large-scale solution to convert CBD to D9-THC, in order to solve several problems today. First, conventional approaches of extracting D9-THC from marijuana are expensive and tedious to maintain due to crop failure. These factors make it incredibly expensive to create D9-THC in a safe and effective manner. Second, greenhouses are expensive to build and maintain. Typical greenhouses cost up to $20 million dollars and only have the capability to produce tens of kilograms of D9-THC a month or season. Traditional methods of converting D9-THC from CBD are plagued by the inability to efficiently produce a high-concentration distillate from pure conversion alone. On top of the concentration limitations, typical conversion problems still apply: racemic mixtures, side products, toxic reagent contamination, low efficiency of starting material, use of flammable chemicals, and many other problems. Economic scalability suffers from these commercial limitations.

SUMMARY OF THE INVENTION

The present invention addresses the aforementioned needs in the art, as will now be summarized and then further described in detail below.

Some variations of the invention provide a process of converting a cannabinoid into a purified cannabinoid derivative, the process comprising:
  (a) providing a starting composition comprising a cannabinoid;
  (b) providing a solvent comprising a $C_9$-$C_{11}$ non-aromatic hydrocarbon;
  (c) introducing the starting composition and the solvent to a conversion reactor;
  (d) operating the conversion reactor at effective reaction conditions to chemically convert the cannabinoid to a cannabinoid derivative at a cannabinoid conversion selected from about 10% to about 90%, thereby generating a reaction mixture containing unreacted cannabinoid;
  (e) conveying the reaction mixture to a crystallization unit;
  (f) within the crystallization unit, cooling the reaction mixture from a first temperature to a second temperature that is lower than the first temperature, to precipitate at least about 50% of the unreacted cannabinoid out of the reaction mixture, thereby generating a mother liquor containing the cannabinoid derivative; and (g) isolating and recovering the cannabinoid derivative from the mother liquor.

Some embodiments provide a process of converting cannabidiol into a purified cannabidiol derivative, the process comprising:
(a) providing a starting composition comprising cannabidiol (CBD);
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the cannabidiol to a cannabidiol derivative at a cannabidiol conversion selected from about 10% to about 90%, thereby generating a reaction mixture containing unreacted cannabidiol;
(e) conveying the reaction mixture to a crystallization unit;
(f) within the crystallization unit, cooling the reaction mixture from a first temperature to a second temperature that is lower than the first temperature, to precipitate at least about 50% of the unreacted cannabidiol out of the reaction mixture, thereby generating a mother liquor containing the cannabidiol derivative; and
(g) isolating and recovering the cannabidiol derivative from the mother liquor.

The starting composition may be obtained from exposing a starting cannabinoid-containing plant material to a process solvent. The process solvent may be supercritical carbon dioxide, for example. In some embodiments, the process solvent is not a $C_9$-$C_{11}$ non-aromatic hydrocarbon or is not n-decane. Alternatively, or additionally, the starting composition may be obtained from an external source, such as from a commercial supplier. Alternatively, or additionally, the starting composition may be obtained from a chemical reaction of a starting cannabinoid-containing plant material, or a starting external source, prior to and separate from step (d), i.e., in a chemical conversion that takes place prior to step (a). A starting cannabinoid-containing plant material may be selected from *Cannabis sativa, Cannabis indica, Cannabis ruderalis, Echinacea purpurea, Echinacea angustifolia, Acmella oleracea, Helichrysum umbraculigerum,* or *Radula marginata.*

In some embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the cannabinoid is cannabidiol. In other certain embodiments, the cannabinoid is cannabigerol.

In some embodiments, the starting composition is characterized by a cannabinoid purity of at least about 90 vol %, at least about 95 vol %, at least about 99 vol %, or essentially 100 vol %. The cannabinoid purity is calculated as mass of the cannabinoid divided by mass of all cannabinoids contained in the starting composition.

During step (c), the cannabinoid/solvent ratio may be selected from about 0.5 to about 2.0, about 0.7 to about 1.3, or about 0.8 to about 1.2, such as about 1.0. The cannabinoid/solvent ratio is calculated as volume of the cannabinoid divided by volume of the $C_9$-$C_{11}$ non-aromatic hydrocarbon solvent.

In various embodiments, the $C_9$-$C_{11}$ non-aromatic hydrocarbon is a $C_{10}$ linear, cyclic, or branched alkane, alkene, or alkyne. In some embodiments, the $C_9$-$C_{11}$ non-aromatic hydrocarbon includes n-decane. In certain embodiments, the $C_9$-$C_{11}$ non-aromatic hydrocarbon consists essentially of n-decane.

In some embodiments, the $C_9$-$C_{11}$ non-aromatic hydrocarbon is a $C_9$ linear, cyclic, or branched alkane, alkene, or alkyne.

In some embodiments, the $C_9$-$C_{11}$ non-aromatic hydrocarbon is a $C_{11}$ linear, cyclic, or branched alkane, alkene, or alkyne.

The starting composition and the solvent may be separately introduced to the conversion reactor. Alternatively, or additionally, the starting composition and the solvent may be blended together and introduced to the conversion reactor.

Step (d) is preferably conducted at reaction conditions effective to chemically convert some, but not all, of the cannabinoid to a cannabinoid derivative, thereby generating a reaction mixture containing unreacted cannabinoid. In some embodiments, the cannabinoid conversion is selected from about 20% to about 80%, such as from about 30% to about 70%, or from about 40% to about 60%, for example. In certain embodiments, the cannabinoid conversion is no greater than 80%, or no greater than 70%, or no greater than 60%, or no greater than 50%.

The effective reaction conditions in step (d) may include a reaction temperature from about −20° C. to about 200° C., a reaction time from about 1 minute to about 120 hours, and/or a reaction pH from about 0.5 to about 12.

The chemical conversion of cannabinoid to cannabinoid derivative may involve solely molecular rearrangement (isomerization) with no elemental addition or retraction. In other embodiments, the chemical conversion of cannabinoid to cannabinoid derivative involves the addition of an element (e.g., hydrogen, carbon, oxygen, or a combination thereof). An example of chemical addition is hydrogenation with $H_2$. In other embodiments, the chemical conversion of cannabinoid to cannabinoid derivative involves the subtraction (elimination) of an element (e.g., carbon, oxygen, hydrogen, or a combination thereof). An example of chemical subtraction is decarboxylation releasing $CO_2$. Combinations of different types of chemical reactions may also occur, simultaneously or sequentially.

In some embodiments, the cannabinoid derivative is an isomer of the cannabinoid. In these embodiments, the effective reaction conditions may include the use of an isomerization catalyst (e.g., an enzyme).

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. When the hydrogenation catalyst is disposed on a catalyst support, the catalyst support may be selected from the group consisting of activated carbon, alumina, silica, aluminosilicate, and combinations thereof.

When hydrogenation is employed, the hydrogenation may convert a cannabinoid into a hydrogenated cannabinoid. Alternatively, or additionally, the hydrogenation may convert a cannabinoid derivative into a hydrogenated cannabinoid derivative.

In certain embodiments, the cannabinoid derivative is selected from D8-THC, D8-THCa, D8-iso-THC, D9-THC, D9-THCa, or a combination thereof, and the hydrogenated cannabinoid derivative is HHC. That HHC may chemically be a racemic mixture in various ratios of 9R-HHC and 9S-HHC. A ratio of the 9R-HHC to the 9S-HHC may be controlled by selecting the hydrogenation catalyst, the hydrogenation reaction conditions, and/or a ratio of (D8-THC+D8-THCa+D8-iso-THC) to (D9-THC+D9-THCa), which may be referred to as a D8-THC/D9-THC ratio.

In some embodiments, the process further comprises filtering and recycling the hydrogenation catalyst. The hydrogenation catalyst may be regenerated or reactivated prior to recycling, if needed.

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt (e.g., calcium acetate)

The effective reaction conditions in step (d) may include exposure to an acid catalyst, such as an aprotic Lewis acid. In some embodiments, an acid catalyst is selected from the group consisting of phosphoric acid, p-toluenesulfonic acid, citric acid, metal chlorides, metal bromides, metal fluorides, iodine-based acids, and combinations thereof. An exemplary acid catalyst is zinc bromide, which is an aprotic Lewis acid. In certain embodiments, the acid catalyst is an aluminosilicate, which may be in the form of molecular sieves.

In some embodiments, the conversion reactor is a packed-bed reactor. The packed-bed reactor may contain a packing material comprising an acid catalyst. Alternatively, or additionally, the packed-bed reactor may contain a packing material comprising molecular sieves, such as to absorb water. When the packed-bed reactor contains a packing material comprising an acid catalyst as well as molecular sieves, the acid catalyst and the molecular sieves may be mixed together. Alternatively, the packed-bed reactor may contains a plurality of chamber, wherein at least a first chamber contains a first packing material comprising molecular sieves, and wherein at least a second chamber contains a second packing material comprising an acid catalyst (the second packing material optionally further comprises additional molecular sieves).

In some embodiments, the crystallization unit in step (f) is a Nutsche unit. The first temperature may be selected from about 20° C. to about 170° C., such as from about 30° C. to about 100° C., for example. The second temperature may be selected from about −20° C. to about 150° C., such as from about −10° C. to about 100° C., or from about 0° C. to about 50° C., for example. The temperature difference between the first temperature and the second temperature may from about 10° C. to about 200° C., such as from about 20° C. to about 100° C., as an measure of the degree of cooling of the reaction mixture in the crystallization unit.

In some embodiments, at least about 75%, 85%, 90%, or 95% of the unreacted cannabinoid is precipitated out of the reaction mixture.

In some embodiments, the cannabinoid derivative is recovered in a product that contains at least 50 vol % of the cannabinoid derivative. This means that the product composition is at least 50 vol % cannabinoid derivative. In some preferred embodiments, the cannabinoid derivative is recovered in a product that contains at least 75 vol %, or at least 90 vol %, of the cannabinoid derivative.

Step (g) may include separating the cannabinoid derivative from the mother liquor by utilizing a compressed gas, such as compressed air.

The process preferably further comprises recovering the solvent. The solvent may be recovered via vacuum extraction, for example. Some or all of the recovered solvent is preferably recycled back to step (b).

In some embodiments, the unreacted cannabinoid that is precipitated in step (f) is washed to remove residual cannabinoid derivative. Whether or not the unreacted and precipitated cannabinoid is washed, the precipitated cannabinoid from step (f) may be reused in step (a) as at least a portion of the starting composition.

In embodiments employing a Nutsche unit as the crystallization unit, the unreacted cannabinoid that is precipitated in step (f) may be recovered using a mesh screen disposed within the Nutsche unit. This configuration enables continuous or semi-continuous recovery of the precipitated cannabinoid.

In some embodiments, the process further comprises chromatographic purification of the cannabinoid derivative between step (f) and step (g), as part of step (g), or following step (g).

In various embodiments, step (g) or another process step utilizes evaporation, distillation, filtration, chromatography, membrane separation, or a combination thereof.

The cannabinoid derivative may be selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof (e.g., HHC), acetylated variants thereof (e.g., D8-THC-O-acetate), and combinations of the foregoing.

In certain embodiments, the cannabinoid derivative includes D9-THC or consists essentially of D9-THC.

There may be a single cannabinoid derivative or multiple cannabinoid derivatives that are produced by the disclosed processes. Also, there may be various reaction intermediates, such as CBDa (cannabidiolic acid) produced from CBD, which CBDa is, in turn, converted to one or more other cannabinoid derivatives. Generally speaking, there may be a reaction network with a plurality of reactants, reaction intermediates, and products (cannabinoid derivatives) with an intermediate or final product distribution dictated by reaction kinetics, chemical equilibrium, mass-transfer rates, or a combination thereof.

The process is preferably continuous or semi-continuous. In some embodiments, some, but not all, steps are continuous or semi-continuous. For example, steps (d), (e), and (f) may be continuous while other steps are in batch or semi-batch mode. In certain embodiments, the entire process is conducted in batch or semi-batch mode.

The present invention also provides a cannabinoid derivative product produced by a process as disclosed.

Other variations of the invention provide a system for converting a cannabinoid into a purified cannabinoid derivative, the system comprising:

a conversion reactor configured with at least one inlet for a starting composition comprising a cannabinoid as well as a solvent comprising a $C_9$-$C_{11}$ non-aromatic hydrocarbon, wherein the conversion reactor is configured to chemically convert some, but not all, of the cannabinoid to a cannabinoid derivative at a cannabinoid conversion, thereby generating a reaction mixture containing unreacted cannabinoid;

a crystallization unit in flow communication with the conversion reactor, wherein the crystallization unit is configured to cool the reaction mixture to precipitate unreacted cannabinoid out of the reaction mixture, thereby generating a mother liquor containing the cannabinoid derivative;

a solvent recovery unit in flow communication with the crystallization unit, wherein the solvent recovery unit is configured to remove the solvent from the mother liquor to generate a purified cannabinoid derivative; and one or more heat exchangers configured to heat and/or cool the conversion reactor, the crystallization unit, and/or the solvent recovery unit.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include n-decane, or consist essentially of n-decane, for example.

The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne.

In some systems, the conversion reactor is a packed-bed reactor. The packed-bed reactor may contain a packing material comprising an acid catalyst, such as an aprotic Lewis acid (e.g., zinc bromide). In various systems, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is an aluminosilicate, which may be in the form of molecular sieves.

The packed-bed reactor (if present) may contains a packing material comprising molecular sieves. In some embodiments, a packed-bed reactor contains a packing material comprising an acid catalyst as well as molecular sieves, wherein the acid catalyst and the molecular sieves are optionally mixed together. In certain embodiments, the packed-bed reactor contains a plurality of chambers, wherein at least a first chamber contains a first packing material comprising molecular sieves, and wherein at least a second chamber contains a second packing material comprising an acid catalyst and possibly additional molecular sieves.

In some systems, the crystallization unit is a Nutsche unit. A Nutsche unit may include a mesh screen configured for recovering precipitated, unreacted cannabinoid.

In some systems, the solvent recovery unit is configured to recover the solvent using a compressed gas, such as compressed air. The solvent recovery unit may be a vacuum extraction unit.

The system may further include a chromatographic purification unit configured to purify the cannabinoid derivative. The chromatographic purification unit may be disposed between the crystallization unit and the solvent recovery unit. Alternatively, the chromatographic purification unit may be disposed between the solvent recovery unit and a product storage tank or container.

In various system embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In various system embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof. In particular embodiments, the cannabinoid derivative includes D9-THC or consists essentially of D9-THC.

The system is preferably configured to operate continuously or semi-continuously. The system is preferably automated using a programmable logic controller.

Other variations of the invention provide a process of converting a terpene into a purified terpene derivative, the process comprising:

(a) providing a starting composition comprising a terpene;

(b) providing a solvent comprising a $C_9$-$C_{11}$ non-aromatic hydrocarbon;

(c) introducing the starting composition and the solvent to a conversion reactor;

(d) operating the conversion reactor at effective reaction conditions to chemically convert the terpene to a terpene derivative at a terpene conversion selected from about 10% to about 90%, thereby generating a reaction mixture containing unreacted terpene;

(e) conveying the reaction mixture to a crystallization unit;

(f) within the crystallization unit, cooling the reaction mixture from a first temperature to a second temperature that is lower than the first temperature, to precipitate at least about 50% of the unreacted terpene out of the reaction mixture, thereby generating a mother liquor containing the terpene derivative; and (g) isolating and recovering the terpene derivative from the mother liquor.

In some embodiments, the terpene is selected from the group consisting of α-pinene, β-pinene, β-thujone, 3-carene, terpinolene, limonene, terpineol, 1,8-cineole, α-terpinene, linalool, myrcene, β-ocimene, α-elemol, β-farnesol, β-farnesene, bisabolol, α-bergamotene, δ-cadinene, γ-eudesmol, valencene, eremophilene, β-himachalene, α-guaiene, germacrene, alloaromadendrene, β-caryophyllene, α-humulene, ocimene, δ-selinene, and combinations thereof.

The starting composition may be obtained from exposing a starting terpene-containing plant material to a process solvent, such as supercritical carbon dioxide. In some embodiments, the process solvent is not a $C_9$-$C_{11}$ non-aromatic hydrocarbon or is not n-decane. Alternatively, or additionally, the starting composition may be obtained from a chemical reaction of a starting terpene-containing plant material, or a starting external source, prior to and separate from step (d), i.e., in a chemical conversion that takes place prior to step (a). A starting terpene-containing plant material may be selected from *Cannabis sativa, Cannabis indica, Cannabis ruderalis, Echinacea purpurea, Echinacea angustifolia, Acmella oleracea, Helichrysum umbraculigerum*, or *Radula marginata*.

In some embodiments related to terpenes, the starting composition is characterized by a terpene concentration of at least about 50 vol %, wherein the terpene concentration is calculated as mass of the terpene divided by mass of all terpenes contained in the starting composition.

In some embodiments, during step (c), a terpene/solvent ratio is selected from about 0.5 to about 2.0, calculated as volume of the terpene divided by volume of the $C_9$-$C_{11}$ non-aromatic hydrocarbon solvent. The terpene/solvent ratio may be selected from about 0.7 to about 1.3, such as about 0.8 to about 1.2, for example.

In some processes related to terpenes, the $C_9$-$C_{11}$ non-aromatic hydrocarbon is a $C_{10}$ linear, cyclic, or branched alkane, alkene, or alkyne. In certain embodiments, the $C_9$-$C_{11}$ non-aromatic hydrocarbon includes n-decane, or consists essentially of n-decane. The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne. Combinations of $C_9$-$C_{11}$ non-aromatic hydrocarbons may be utilized in the solvent.

The starting composition and the solvent may be separately introduced to the conversion reactor. Alternatively, or additionally, the starting composition and the solvent may be blended together and introduced to the conversion reactor.

Step (d) is preferably conducted at reaction conditions effective to chemically convert some, but not all, of the terpene to a terpene derivative, thereby generating a reaction mixture containing unreacted terpene. In some embodiments, the terpene conversion is selected from about 20% to about 80%, such as from about 30% to about 70%, or from about 40% to about 60%, for example. In certain embodiments, the terpene conversion is no greater than 80%, or no greater than 70%, or no greater than 60%, or no greater than 50%.

In processes relating to terpenes, the effective reaction conditions in step (d) may include a reaction temperature from about −20° C. to about 200° C., a reaction time from about 1 minute to about 120 hours, and/or a reaction pH from about 0.5 to about 12.

In some embodiments, a terpene derivative is an isomer of a terpene.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. The optional catalyst support may be selected from the group consisting of activated carbon, alumina, silica, aluminosilicate, and combinations thereof. The hydrogenation catalyst may be filtered and recycled.

In some embodiments, hydrogenation converts a terpene into a hydrogenated terpene. In these or other embodiments, hydrogenation converts a terpene derivative into a hydrogenated terpene derivative.

In some embodiments, the effective reaction conditions include acetylation of the terpene with acetic acid or an acetate salt. In these or other embodiments, the effective reaction conditions include acetylation of the terpene derivative with acetic acid or an acetate salt.

The effective reaction conditions in step (d) may include exposure to an acid catalyst, such as an aprotic Lewis acid. In some embodiments, an acid catalyst is selected from the group consisting of phosphoric acid, p-toluenesulfonic acid, citric acid, metal chlorides, metal bromides, metal fluorides, iodine-based acids, and combinations thereof. An exemplary acid catalyst is zinc bromide, which is an aprotic Lewis acid. In certain embodiments, the acid catalyst is an aluminosilicate, which may be in the form of molecular sieves.

In some embodiments related to terpenes, the conversion reactor is a packed-bed reactor. The packed-bed reactor may contain a packing material comprising an acid catalyst. Alternatively, or additionally, the packed-bed reactor may contain a packing material comprising molecular sieves, such as to absorb water. When the packed-bed reactor contains a packing material comprising an acid catalyst as well as molecular sieves, the acid catalyst and the molecular sieves may be mixed together. Alternatively, the packed-bed reactor may contains a plurality of chamber, wherein at least a first chamber contains a first packing material comprising molecular sieves, and wherein at least a second chamber contains a second packing material comprising an acid catalyst (the second packing material optionally further comprises additional molecular sieves).

In some embodiments related to terpenes, the crystallization unit in step (f) is a Nutsche unit. The first temperature may be selected from about 20° C. to about 170° C., such as from about 30° C. to about 100° C., for example. The second temperature may be selected from about −20° C. to about 150° C., such as from about −10° C. to about 100° C., or from about 0° C. to about 50° C., for example. The temperature difference between the first temperature and the second temperature may from about 10° C. to about 200° C., such as from about 20° C. to about 100° C., as an measure of the degree of cooling of the reaction mixture in the crystallization unit.

In some embodiments, at least about 75%, 85%, 90%, or 95% of the unreacted terpene is precipitated out of the reaction mixture.

In some embodiments, the terpene derivative is recovered in a product that contains at least 50 vol % of the terpene derivative. This means that the product composition is at least 50 vol % terpene derivative. In some preferred embodiments, the terpene derivative is recovered in a product that contains at least 75 vol %, or at least 90 vol %, of the terpene derivative.

Step (g) may include separating the terpene derivative from the mother liquor by utilizing a compressed gas, such as compressed air.

The process preferably further comprises recovering the solvent. The solvent may be recovered via vacuum extraction, for example. Some or all of the recovered solvent is preferably recycled back to step (b).

In some embodiments, the unreacted terpene that is precipitated in step (f) is washed to remove residual terpene derivative. Whether or not the unreacted and precipitated terpene is washed, the precipitated terpene from step (f) may be reused in step (a) as at least a portion of the starting composition.

In embodiments employing a Nutsche unit as the terpene crystallization unit, the unreacted terpene that is precipitated in step (f) may be recovered using a mesh screen disposed within the Nutsche unit. This configuration enables continuous or semi-continuous recovery of the precipitated terpene.

In some embodiments, the process further comprises chromatographic purification of the terpene derivative between step (f) and step (g), as part of step (g), or following step (g).

The terpene derivative may be a cannabinoid selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

The terpene derivative may be selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof.

In certain embodiments, the terpene derivative includes D9-THC or consists essentially of D9-THC.

There may be a single terpene derivative or multiple terpene derivatives that are produced by the disclosed processes. Also, there may be various reaction intermediates which are then converted to one or more other terpene derivatives. Generally speaking, there may be a reaction network with a plurality of reactants, reaction intermediates, and products (terpene derivatives) with an intermediate or final product distribution dictated by reaction kinetics, chemical equilibrium, mass-transfer rates, or a combination thereof.

The process is preferably continuous or semi-continuous. In some embodiments, some, but not all, steps are continuous or semi-continuous. For example, steps (d), (e), and (f) may be continuous while other steps are in batch or semi-batch mode. In certain embodiments, the entire process is conducted in batch or semi-batch mode.

The present invention also provides a terpene derivative product produced by a process as disclosed.

Still other variations of the invention provide a system for converting a terpene into a purified terpene derivative, the system comprising:

a conversion reactor configured with at least one inlet for a starting composition comprising a terpene as well as a solvent comprising a $C_9$-$C_{11}$ non-aromatic hydrocarbon, wherein the conversion reactor is configured to chemically convert some, but not all, of the terpene to a terpene derivative at a terpene conversion, thereby generating a reaction mixture containing unreacted terpene;

a crystallization unit in flow communication with the conversion reactor, wherein the crystallization unit is configured to cool the reaction mixture to precipitate unreacted terpene out of the reaction mixture, thereby generating a mother liquor containing the terpene derivative;

a solvent recovery unit in flow communication with the crystallization unit, wherein the solvent recovery unit is configured to remove the solvent from the mother liquor to generate a purified terpene derivative; and one or more heat exchangers configured to heat and/or cool the conversion reactor, the crystallization unit, and/or the solvent recovery unit.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include n-decane, or consist essentially of n-decane, for example.

The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne.

In some systems relating to terpenes, the conversion reactor is a packed-bed reactor. The packed-bed reactor may contain a packing material comprising an acid catalyst, such as an aprotic Lewis acid (e.g., zinc bromide). In various systems, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is an aluminosilicate, which may be in the form of molecular sieves.

The packed-bed reactor (if present) may contains a packing material comprising molecular sieves. In some embodiments, a packed-bed reactor contains a packing material comprising an acid catalyst as well as molecular sieves, wherein the acid catalyst and the molecular sieves are optionally mixed together. In certain embodiments, the packed-bed reactor contains a plurality of chambers, wherein at least a first chamber contains a first packing material comprising molecular sieves, and wherein at least a second chamber contains a second packing material comprising an acid catalyst and possibly additional molecular sieves.

In some systems, the terpene crystallization unit is a Nutsche unit. A Nutsche unit may include a mesh screen configured for recovering precipitated, unreacted terpene.

In some systems, the solvent recovery unit is configured to recover the solvent using a compressed gas, such as compressed air. The solvent recovery unit may be a vacuum extraction unit.

The system may further include a chromatographic purification unit configured to purify the terpene derivative. The chromatographic purification unit may be disposed between the crystallization unit and the solvent recovery unit. Alternatively, the chromatographic purification unit may be disposed between the solvent recovery unit and a product storage tank or container.

In various systems, the terpene is selected from the group consisting of α-pinene, β-pinene, β-thujone, 3-carene, terpinolene, limonene, terpineol, 1,8-cineole, α-terpinene, linalool, myrcene, β-ocimene, α-elemol, β-farnesol, β-farnesene, bisabolol, α-bergamotene, δ-cadinene, γ-eudesmol, valencene, eremophilene, β-himachalene, α-guaiene, germacrene, alloaromadendrene, β-caryophyllene, α-humulene, ocimene, δ-selinene, and combinations thereof.

In various systems, the terpene derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof. In particular embodiments, the terpene derivative includes D9-THC or consists essentially of D9-THC.

The system is preferably configured to operate continuously or semi-continuously. The system is preferably automated using a programmable logic controller.

Other variations provide a process of converting a cannabinoid into a cannabinoid derivative utilizing a high-temperature conversion reactor, the process comprising:

(a) providing a starting composition comprising a cannabinoid;
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the cannabinoid to a cannabinoid derivative at a cannabinoid conversion selected from about 10% to about 100%, thereby generating a reaction mixture, wherein the effective reaction conditions include a reaction temperature selected from about 100° C. to about 170° C.; and
(e) recovering the cannabinoid derivative from the reaction mixture.

In some embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In certain embodiments, the cannabinoid is cannabidiol. In certain embodiments, the cannabinoid is cannabigerol.

In some embodiments, the starting composition is characterized by a cannabinoid purity of at least about 90 vol %, wherein the cannabinoid purity is calculated as mass of the cannabinoid divided by mass of all cannabinoids contained in the starting composition.

In some embodiments, during step (c), a cannabinoid/solvent ratio is selected from about 0.5 to about 2.0, calculated as volume of the cannabinoid divided by volume of the $C_9$-$C_{11}$ non-aromatic hydrocarbon solvent. The cannabinoid/solvent ratio may be selected from about 0.8 to about 1.2, for example.

In some embodiments, the $C_9$-$C_{11}$ non-aromatic hydrocarbon is a $C_{10}$ linear, cyclic, or branched alkane, alkene, or alkyne. In certain embodiments, the $C_9$-$C_{11}$ non-aromatic hydrocarbon includes n-decane.

In some embodiments, the $C_9$-$C_{11}$ non-aromatic hydrocarbon is a $C_9$ linear, cyclic, or branched alkane, alkene, or alkyne.

In some embodiments, the $C_9$-$C_{11}$ non-aromatic hydrocarbon is a $C_{11}$ linear, cyclic, or branched alkane, alkene, or alkyne.

In some embodiments, the starting composition and the solvent are blended together and introduced to the conversion reactor.

In some embodiments, the reaction temperature is selected from about 100° C. to about 130° C., or from about 130° C. to about 170° C. In some embodiments, the reaction temperature is selected to be below the normal boiling point of the solvent.

In some embodiments, the effective reaction conditions in step (d) include a reaction time from about 1 minute to about 120 hours.

In some embodiments, the effective reaction conditions in step (d) include a reaction pH from about 0.5 to about 12.

In some embodiments, the cannabinoid derivative is an isomer of the cannabinoid. In these embodiments, the effective reaction conditions may include the use of an isomerization catalyst.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. When the hydrogenation catalyst is disposed on a catalyst support, the catalyst support may be selected from the group consisting of activated carbon, alumina, silica, aluminosilicate, and combinations thereof.

When hydrogenation is employed, the hydrogenation may convert a cannabinoid into a hydrogenated cannabinoid. Alternatively, or additionally, the hydrogenation may convert a cannabinoid derivative into a hydrogenated cannabinoid derivative.

In certain embodiments, the cannabinoid derivative is selected from D8-THC, D8-THCa, D8-iso-THC, D9-THC, D9-THCa, or a combination thereof, and the hydrogenated cannabinoid derivative is HHC. That HHC may be a racemic mixture of 9R-HHC and 9S-HHC. A ratio of the 9R-HHC to the 9S-HHC may be controlled by selecting the hydrogenation catalyst, the effective reaction conditions, and/or a ratio of (D8-THC+D8-THCa+D8-iso-THC) to (D9-THC+D9-THCa), which may be referred to as a D8-THC/D9-THC ratio.

In some embodiments, the process further comprises filtering and recycling the hydrogenation catalyst. The hydrogenation catalyst may be regenerated prior to recycling, if needed.

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt.

In some embodiments, the effective reaction conditions in step (d) include exposure to an acid catalyst. The acid catalyst may be an aprotic Lewis acid. In some embodiments, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is zinc bromide. In certain embodiments, the acid catalyst is an aluminosilicate, which may be in the form of molecular sieves.

In some embodiments, the conversion reactor is a packed-bed reactor. The packed-bed reactor may contain a packing material comprising an acid catalyst. The packed-bed reactor may contain a packing material comprising molecular sieves, whether or not the molecular sieves possess catalytic activity. The packed-bed reactor may contain a packing material comprising an acid catalyst as well as molecular sieves, wherein the acid catalyst and the molecular sieves are mixed together. The packed-bed reactor may contain a plurality of chambers, wherein at least a first chamber contains a first packing material comprising molecular sieves, and wherein at least a second chamber contains a second packing material comprising an acid catalyst. The second packing material may further comprise additional molecular sieves.

In some embodiments, step (e) includes exposing the reaction mixture to a flocculant. The flocculant may form a floc comprising the flocculant combined with a reaction byproduct, a solvent emulsion, an impurity, or a combination thereof. In some embodiments, the flocculant is a polysaccharide, such as a polysaccharide selected from the group consisting of chitosan, starch, cellulose, hemicellulose, nanocellulose, polyglucan, glycogen, chitin, glucose oligomers, xylose oligomers, and combinations thereof.

In some embodiments, step (e) includes conveying the reaction mixture to a crystallization unit to purify the cannabinoid derivative. The reaction mixture may be cooled within the crystallization unit from a first temperature to a second temperature that is lower than the first temperature, to precipitate unreacted cannabinoid out of the reaction mixture, thereby generating a mother liquor containing the cannabinoid derivative.

In some embodiments, step (e) includes distilling the reaction mixture to purify the cannabinoid derivative. Distillation may be beneficial to remove color bodies, for example.

In some embodiments, step (e) includes chromatographically purifying the cannabinoid derivative.

Generally, step (e) may utilize evaporation, distillation, filtration, chromatography, membrane separation, or a combination thereof.

In some embodiments, the process further comprises recovering the solvent. The solvent may be recovered via vacuum extraction. The solvent may be recycled back to step (b).

In some embodiments, the starting composition is obtained from an external source. In other embodiments, the starting composition is obtained from exposing a starting cannabinoid-containing plant material to a process solvent (e.g., supercritical $CO_2$, acetone, methanol, and/or ethanol). In some embodiments, the starting composition is obtained from a chemical reaction of a starting cannabinoid-containing plant material, prior to and separate from step (d).

The starting cannabinoid-containing plant material may be selected from *Cannabis sativa*, *Cannabis indica*, *Cannabis ruderalis*, *Echinacea purpurea*, *Echinacea angustifolia*, *Acmella oleracea*, *Helichrysum umbraculigerum*, or *Radula marginata*.

In various embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof, acetylated variants thereof, and combinations of the foregoing.

In some embodiments, the process is continuous or semi-continuous. In other embodiments, the process is a batch or semi-batch process.

Yet other variations provide a process of converting a cannabinoid into a purified cannabinoid derivative utilizing flocculation, the process comprising:
(a) providing a starting composition comprising a cannabinoid;
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the cannabinoid to a cannabinoid derivative at a cannabinoid conversion selected from about 10% to about 100%, thereby generating a reaction mixture;
(e) exposing the reaction mixture to a flocculant; and
(f) isolating and recovering the cannabinoid derivative from the reaction mixture.

The cannabinoid may be selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the cannabinoid is cannabidiol, cannabigerol, or a mixture thereof.

In some embodiments, the starting composition is characterized by a cannabinoid purity of at least about 90 vol %, wherein the cannabinoid purity is calculated as mass of the cannabinoid divided by mass of all cannabinoids contained in the starting composition.

In some processes, during step (c), a cannabinoid/solvent ratio is selected from about 0.5 to about 2.0, calculated as volume of the cannabinoid divided by volume of the $C_9$-$C_{11}$ non-aromatic hydrocarbon solvent. In certain embodiments, during step (c), the cannabinoid/solvent ratio is selected from about 0.8 to about 1.2.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include, or consist essentially of, n-decane.

In some embodiments, the $C_9$-$C_{11}$ non-aromatic hydrocarbon is a $C_9$ linear, cyclic, or branched alkane, alkene, or alkyne.

In some embodiments, the $C_9$-$C_{11}$ non-aromatic hydrocarbon is a $C_{11}$ linear, cyclic, or branched alkane, alkene, or alkyne.

In some embodiments, the starting composition and the solvent are blended together and introduced to the conversion reactor.

In some embodiments, the effective reaction conditions include a reaction temperature selected from about 20° C. to about 170° C., such as from about 50° C. to about 170° C., or from about 100° C. to about 130° C. In certain embodiments, the reaction temperature is selected to be below the normal boiling point of the solvent.

In some embodiments, the effective reaction conditions in step (d) include a reaction time from about 1 minute to about 120 hours.

In some embodiments, the effective reaction conditions in step (d) include a reaction pH from about 0.5 to about 12.

In some embodiments, the cannabinoid derivative is an isomer of the cannabinoid. Isomerization may be catalyzed or uncatalyzed.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. The optional catalyst support may be selected from the group consisting of activated carbon, alumina, silica, aluminosilicate, and combinations thereof.

In some embodiments, hydrogenation converts a cannabinoid into a hydrogenated cannabinoid. In these or other embodiments, the hydrogenation may convert a cannabinoid derivative into a hydrogenated cannabinoid derivative. For example, a cannabinoid derivative selected from D8-THC, D8-THCa, D8-iso-THC, D9-THC, D9-THCa, or a combination thereof, may be hydrogenated into the hydrogenated cannabinoid derivative HHC. That HHC may be a racemic mixture of 9R-HHC and 9S-HHC. A ratio of the 9R-HHC to the 9S-HHC may be controlled by selecting the hydrogenation catalyst, the effective reaction conditions, and/or a ratio of (D8-THC+D8-THCa+D8-iso-THC) to (D9-THC+D9-THCa).

The hydrogenation catalyst may be filtered and recycled, optionally with treatment (e.g., regeneration or reactivation) prior to recycling.

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt.

In some embodiments, the effective reaction conditions in step (d) include exposure to an acid catalyst. The acid catalyst may be an aprotic Lewis acid. In some embodiments, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is zinc bromide. In other embodiments, the acid catalyst is an aluminosilicate, which may be in the form of molecular sieves.

In some embodiments, the conversion reactor is a packed-bed reactor. The packed-bed reactor may contain a packing material comprising an acid catalyst. The packed-bed reactor may contain a packing material comprising molecular sieves. The packed-bed reactor may contain a packing material comprising an acid catalyst as well as molecular sieves, wherein the acid catalyst and the molecular sieves are mixed together. The packed-bed reactor may contain a plurality of chambers, wherein at least a first chamber contains a first packing material comprising molecular sieves, and wherein at least a second chamber contains a second packing material comprising an acid catalyst. The second packing material may further comprise additional molecular sieves.

In some embodiments, the flocculant forms a floc comprising the flocculant combined with a reaction byproduct, a solvent emulsion, an impurity, or a combination thereof. The flocculant may be a polysaccharide. The polysaccharide may be selected from the group consisting of chitosan, starch, cellulose, hemicellulose, nanocellulose, polyglucan, glycogen, chitin, glucose oligomers, xylose oligomers, and combinations thereof. In certain embodiments, the flocculant is chitosan.

In some embodiments, the process further comprises conveying the reaction mixture to a crystallization unit, in step (e) or step (f). The reaction mixture may be cooled within the crystallization unit from a first temperature to a second temperature that is lower than the first temperature, to precipitate unreacted cannabinoid out of the reaction mixture, thereby generating a mother liquor containing the cannabinoid derivative.

In some embodiments, step (f) includes distilling the reaction mixture to purify the cannabinoid derivative.

In some embodiments, step (f) includes chromatographically purifying the cannabinoid derivative.

In various embodiments, step (0 utilizes evaporation, distillation, filtration, chromatography, membrane separation, or a combination thereof.

In some embodiments, the process further comprises recovering the solvent. The solvent may be recovered via vacuum extraction. The recovered solvent may be recycled back to step (b).

In some embodiments, the starting composition is obtained from an external source. In other embodiments, the starting composition is obtained from exposing a starting cannabinoid-containing plant material to a process solvent (e.g., supercritical $CO_2$). The starting composition may be obtained from a chemical reaction of a starting cannabinoid-containing plant material, prior to and separate from step (d).

The starting cannabinoid-containing plant material may be selected from *Cannabis sativa, Cannabis indica, Cannabis ruderalis, Echinacea purpurea, Echinacea angustifolia, Acmella oleracea, Helichrysum umbraculigerum,* or *Radula marginata.*

In some embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof, acetylated variants thereof, and combinations of the foregoing.

In some embodiments, the process is continuous or semi-continuous. In other embodiments, the process is a batch or semi-batch process.

DETAILED DESCRIPTION OF EMBODIMENTS OF THE INVENTION

Figure 1:
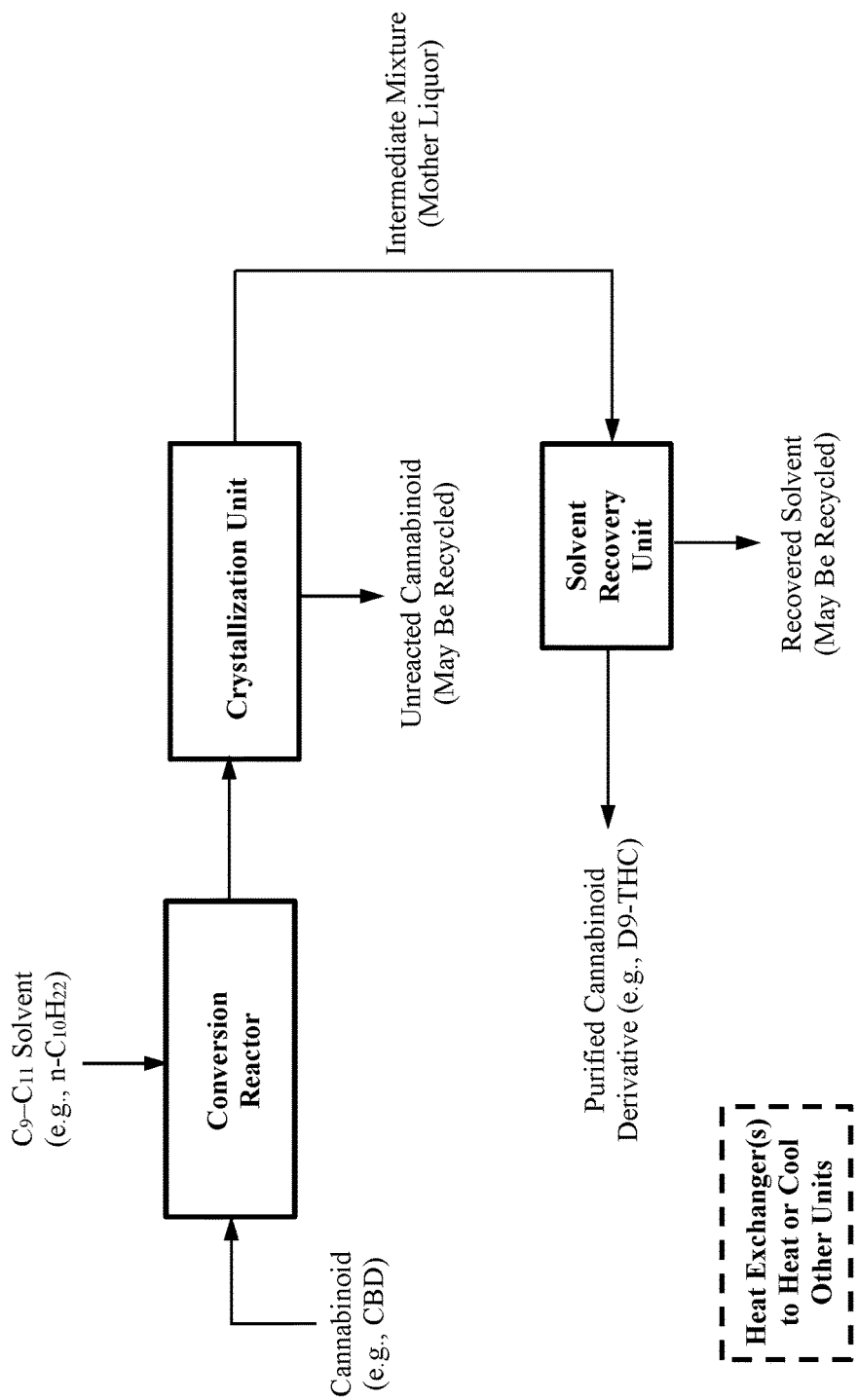
FIG. 1 is an exemplary block-flow diagram of a process and system for converting a cannabinoid into a purified cannabinoid derivative, in some embodiments.

The processes and systems of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in Markush groups. Thus in some embodiments not otherwise explicitly recited, any instance of "comprising" may be replaced by "consisting of" or, alternatively, by "consisting essentially of."

Variations of the invention are predicated on the discovery of a surprisingly effective solvent for the recovery of cannabinoid derivatives and/or terpene derivatives from plant extracts. As will become apparent in this specification, there are many cannabinoid derivatives and/or terpene derivatives that may be generated, starting with cannabinoids and/or terpenes.

An exemplary embodiment converts the cannabinoid CBD (i.e., cannabidiol) into D9-THC. In this patent application, "D9-THC" refers to (−)-trans-$\Delta^9$-tetrahydrocannabinol, (−)-cis-$\Delta^9$-tetrahydrocannabinol, (+)-trans-$\Delta^9$-tetrahydrocannabinol, (+)-cis-$\Delta^9$-tetrahydrocannabinol, or a mixture of two or more of the foregoing. (+) and (−) refer to optical isomers, also known as enantiomers. Trans and cis refer to configurational isomers. Cis-trans isomers are stereoisomers—pairs of molecules which have the same formula but whose functional groups are in different orientations in three-dimensional space.

The inventor has experimented with various solvents and temperatures to discover which solvents work most effectively, in some embodiments. It has been found that $C_9$ to $C_{11}$ non-aromatic hydrocarbon solvents, and especially n-decane, work very well. Unlike lower alkanes such as pentane, n-decane does not easily combust at normal operating conditions. As the molecular size of an alkane increases, the percentage of carbon in the alkane molecules also increases. As a result, alkanes become less flammable with higher carbon number. Nonane (n-$C_9H_{20}$) is the lightest alkane to have a flash point above 25° C., and for this reason nonane is not classified as dangerously flammable whereas all alkanes $C_8$ and smaller are classified as dangerously flammable. Because of this important threshold, "higher alkanes" are often defined as alkanes having nine or more carbon atoms.

It has also been found experimentally that unlike pentane and n-heptane, n-decane is capable of causing cannabinoid precipitation at room temperature (about 25° C.) with ease and high efficiency. Precipitation at relatively high temperatures, rather than very low temperatures (e.g., −50° C.), has a positive impact on the economics. See Example 1 herein, showing an efficiency of 90% using n-decane as the solvent for precipitation. Comparatively, pentane and n-heptane only reach a maximum efficiency of 70%, but to do so the mixture must be brought down to −50° C., which is uneconomical. Decane leads to more efficient results at a much higher temperature (up to room temperature or even higher) which is a significant economic advantage.

Further experimentation has shown that there is an optimum of 9 to 11 carbon atoms in the solvent molecule. For example, the linear alkane containing 12 carbons, n-dodecane (n-$C_{12}H_{26}$), resulted in poor ability to precipitate cannabinoids. Therefore, there is an unexpected sweet spot of $C_9$ to $C_{11}$ non-aromatic hydrocarbon solvents that are superior to both $C_{8-}$ hydrocarbons as well as $C_{12+}$ hydrocarbons. Without being limited by speculation, it is believed that there is an interplay of variations in electron density of the solvent molecule, causing relatively high dipole moments across the molecule, with other intrinsic properties of hydrocarbons. For example, the boiling points of alkanes increase with increasing number of carbons. This is because the intermolecular attractive forces, although individually weak, become cumulatively more significant as the number of atoms and electrons in the molecule increases. In addition to polarity and intermolecular forces, there are differences in chemical properties including viscosity with varying numbers of carbon atoms. As the number of carbons increases, the viscosity increases, which theoretically will reduce solute mass-transfer rates in the solvent (lower Reynolds number) which in turn may reduce crystallization kinetics, potentially explaining why n-dodecane does not work as well. For small numbers of carbon atoms (e.g., 5 in pentane), while viscosity may be acceptable, the solute solubility is too high and precipitation is inefficient unless the temperature is very low. It is apparent that there are competing effects, resulting in $C_9$-$C_{11}$ being the optimum. The present invention is not, however, limited to theories or reasons why $C_9$ to $C_{11}$ non-aromatic hydrocarbon solvents are particularly effective.

Some variations of the invention provide a process of converting a cannabinoid into a purified cannabinoid derivative, the process comprising:
(a) providing a starting composition comprising a cannabinoid;
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the cannabinoid to a cannabinoid derivative at a cannabinoid conversion selected from about 10% to about 90%, thereby generating a reaction mixture containing unreacted cannabinoid;
(e) conveying the reaction mixture to a crystallization unit;
(f) within the crystallization unit, cooling the reaction mixture from a first temperature to a second temperature that is lower than the first temperature, to precipitate at least about 50% of the unreacted cannabinoid out of the reaction mixture, thereby generating a mother liquor containing the cannabinoid derivative; and
(g) isolating and recovering the cannabinoid derivative from the mother liquor.

Certain embodiments provide a process of converting cannabidiol into a purified cannabidiol derivative, the process comprising:
(a) providing a starting composition comprising cannabidiol (CBD);
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the cannabidiol to a cannabidiol derivative at a cannabidiol conversion selected from about 10% to about 90%, thereby generating a reaction mixture containing unreacted cannabidiol;
(e) conveying the reaction mixture to a crystallization unit;
(f) within the crystallization unit, cooling the reaction mixture from a first temperature to a second temperature that is lower than the first temperature, to precipitate at least about 50% of the unreacted cannabidiol out of the reaction mixture, thereby generating a mother liquor containing the cannabidiol derivative; and
(g) isolating and recovering the cannabidiol derivative from the mother liquor.

The starting composition may be obtained from exposing a starting cannabinoid-containing plant material to a process solvent. The process solvent may be supercritical carbon dioxide, for example. In some embodiments, the process solvent is not a $C_9$-$C_{11}$ non-aromatic hydrocarbon or is not n-decane. The process solvent may be a hydrocarbon, such as a $C_2$-$C_8$ alkane. The process solvent may be a $C_1$-$C_{12}$ alcohol, such as ethanol.

Alternatively, or additionally, the starting composition may be obtained from an external source, such as from a commercial supplier. Alternatively, or additionally, the starting composition may be obtained from a chemical reaction of a starting cannabinoid-containing plant material, or a starting external source, prior to and separate from step (d), i.e., in a chemical conversion that takes place prior to step (a). A starting cannabinoid-containing plant material may be selected from *Cannabis sativa, Cannabis indica, Cannabis ruderalis, Echinacea purpurea, Echinacea angustifolia, Acmella oleracea, Helichrysum umbraculigerum*, or *Radula marginata*.

In typical embodiments, the cannabinoid-containing plant material is selected from the *Cannabis* genus, including the specific species *Cannabis sativa, Cannabis indica*, and *Cannabis ruderalis*. Phytocannabinoids are known to occur in several plant species besides *Cannabis*. These include *Echinacea purpurea, Echinacea angustifolia, Acmella oleracea, Helichrysum umbraculigerum*, and *Radula marginata*. Well-known cannabinoids that are not derived from Cannabis are lipophilic alkylamides from *Echinacea* species, most notably dodeca-2E,4E,8Z,10E/Z-tetraenoic acid isobutylamide.

In some embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the cannabinoid is cannabidiol. In other certain embodiments, the cannabinoid is cannabigerol.

In some embodiments, the starting composition is characterized by a cannabinoid purity of at least about 90 vol %, at least about 95 vol %, at least about 99 vol %, or essentially 100 vol %. The cannabinoid purity is calculated as mass of the cannabinoid divided by mass of all cannabinoids contained in the starting composition.

During step (c), the cannabinoid/solvent ratio may be selected from about 0.5 to about 2.0, about 0.7 to about 1.3, or about 0.8 to about 1.2, such as about 1.0. The cannabinoid/solvent ratio is calculated as volume of the cannabinoid divided by volume of the $C_9$-$C_{11}$ non-aromatic hydrocarbon solvent.

In various embodiments, the $C_9$-$C_{11}$ non-aromatic hydrocarbon is a $C_{10}$ linear, cyclic, or branched alkane, alkene, or alkyne. In some embodiments, the $C_9$-$C_{11}$ non-aromatic hydrocarbon includes n-decane. In certain embodiments, the $C_9$-$C_{11}$ non-aromatic hydrocarbon consists essentially of n-decane. When the $C_9$-$C_{11}$ non-aromatic hydrocarbon is a single molecule such as n-decane, reference may be made to a "mono-solvent design" of the purification process.

The $C_9$-$C_{11}$ non-aromatic hydrocarbon is a crystallization-inducing solvent. By "crystallization-inducing" it is meant that the solvent is capable of causing precipitation of unreacted cannabinoids or unreacted terpenes. Generally, $C_9$-$C_{11}$ non-aromatic hydrocarbons may be alkanes (only single C—C bonds present), alkenes (one or more C═C double bonds present), or alkynes (one or more C≡C triple bonds present) and may be linear, cyclic, or branched.

In some embodiments, the solvent is a $C_{10}$ non-aromatic hydrocarbon solvent. Especially preferred are $C_{10}$ alkanes, which are decane and any of its isomers. That is, in preferred embodiments, the solvent is selected from the group consisting of n-decane, 2-methylnonane, 3-methylnonane, 4-methylnonane, 5-methylnonane, 3-ethyloctane, 4-ethyloctane, 2,2-dimethyloctane, 2,3-dimethyloctane, 2,4-dimethyloctane, 2,5-dimethyloctane, 2,6-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, 4-propylheptane, 4-isopropylheptane, 2-methyl-3-ethylheptane, 2-methyl-4-ethylheptane, 2-methyl-5-ethylheptane, 3-methyl-3-ethylheptane, 3-methyl-4-ethylheptane, 3-methyl-5-ethylheptane, 4-methyl-3-ethylheptane, 4-methyl-4-ethylheptane, 2,2,3-trimethylheptane, 2,2,4-trimethylheptane, 2,2,5-trimethylheptane, 2,2,6-trimethylheptane, 2,3,3-trimethylheptane, 2,3,4-trimethylheptane, 2,3,5-trimethylheptane, 2,3,6-trimethylheptane, 2,4,4-trimethylheptane, 2,4,5-trimethylheptane, 2,4,6-trimethylheptane, 2,5,5-trimethylheptane, 3,3,4-trimethylheptane, 3,3,5-trimethylheptane, 3,4,4-trimethylheptane, 3,4,5-trimethylheptane, 2-methyl isopropylhexane, 3,3-diethylhexane, 3,4-diethylhexane, 2,2-dimethyl-3-ethylhexane, 2,2-dimethyl-4-ethylhexane, 2,3-dimethyl-3-ethylhexane, 2,3-dimethyl-4-ethylhexane, 2,4-dimethyl-3-ethylhexane, 2,4-dimethyl-4-ethylhexane, 2,5-dimethyl-3-ethylhexane, 3,3-dimethyl-4-ethylhexane, 3,4-dimethyl-3-ethylhexane, 2,2,3,3-tetramethylhexane, 2,2,3,4-tetramethylhexane, 2,2,3,5-tetramethylhexane, 2,2,4,4-tetramethylhexane, 2,2,4,5-tetramethylhexane, 2,2,5,5-tetramethylhexane, 2,3,3,4-tetramethylhexane, 2,3,3,5-tetramethylhexane, 2,3,4,4-tetramethylhexane, 2,3,4,5-tetramethylhexane, 3,3,4,4-tetramethylhexane, 2,4-dimethyl-3-isopropylpentane, 2-methyl-3,3-diethylpentane, 2,2,3-trimethyl-3-ethylpentane, 2,2,4-trimethyl-3-ethylpentane, 2,3,4-trimethyl-3-ethylpentane, 2,2,3,3,4-pentamethylpentane, 2,2,3,4,4-pentamethylpentane, and combinations thereof. In certain preferred embodiments, the solvent is specifically n-decane, n-$C_{10}H_{22}$, or is a solvent comprising n-decane.

In some embodiments, the $C_9$-$C_{11}$ non-aromatic hydrocarbon solvent is a $C_{10}$ linear, cyclic, or branched alkane solvent. Linear or branched $C_{10}$ alkanes generally have the formula $C_{10}H_{22}$, while cyclic $C_{10}$ alkanes have less hydrogen (e.g., cyclodecane is $C_{10}H_{20}$).

In some embodiments, the $C_9$-$C_{11}$ non-aromatic hydrocarbon solvent is a $C_{10}$ linear, cyclic, or branched alkene solvent. An alkene contains at least one carbon-carbon double bond, C═C. Exemplary $C_{10}$ alkenes are 1-decene or 4-decene, for instance. Linear or branched $C_{10}$ single alkenes generally have the formula $C_{10}H_{20}$, while cyclic $C_{10}$ alkenes have less hydrogen.

In some embodiments, the $C_9$-$C_{11}$ non-aromatic hydrocarbon solvent is a $C_{10}$ linear, cyclic, or branched alkyne solvent. An alkyne contains at least one carbon-carbon triple bond, C≡C. Exemplary $C_{10}$ alkynes are 1-decyne and 2-decyne, for instance. Linear or branched $C_{10}$ single alkynes generally have the formula $C_{10}H_{18}$, while cyclic $C_{10}$ alkynes have less hydrogen.

In some embodiments, the $C_9$-$C_{11}$ non-aromatic hydrocarbon solvent is a $C_9$ linear, cyclic, or branched alkane solvent, a $C_9$ linear, cyclic, or branched alkene solvent, a $C_9$ linear, cyclic, or branched alkyne solvent, or a combination thereof. Examples of $C_9$ solvents include n-nonane, 1-nonene, 1-nonyne, and bicyclo[3.3.1]nonane. Linear and branched $C_9$ alkanes generally have the formula $C_9H_{20}$, linear and branched $C_9$ single alkenes generally have the formula $C_9H_{18}$, and linear and branched $C_9$ single alkynes generally have the formula $C_9H_{16}$.

In some embodiments, the $C_9$-$C_{11}$ non-aromatic hydrocarbon solvent is a $C_{11}$ linear, cyclic, or branched alkane solvent, a $C_{11}$ linear, cyclic, or branched alkene solvent, a $C_{11}$ linear, cyclic, or branched alkyne solvent, or a combination thereof. Examples of $C_{11}$ solvents include n-undecane, 5-undecene, and 3-undecyne. Linear and branched $C_{11}$ alkanes generally have the formula $C_{11}H_{24}$, linear and branched $C_{11}$ single alkenes generally have the formula $C_{11}H_{22}$, and linear and branched $C_{11}$ single alkynes generally have the formula $C_{11}H_{20}$.

In this disclosure, "cyclic" also includes polycyclic structures, such as bicyclo structures. Bicyclo compounds are a class of saturated compounds consisting of two fused rings, having two or more atoms in common, and that take the name of an open-chain hydrocarbon containing the same total number of atoms. Examples include bicyclo[6.1.1] decane, $C_{10}H_{18}$ and 2-methylbicyclo[4.2.2]decane, $C_{11}H_{20}$.

$C_9$ to $C_{11}$ aromatic hydrocarbon solvents (e.g., n-butylbenzene, $C_{10}H_{14}$) are not expected to work as well as $C_9$ to $C_{11}$ non-aromatic hydrocarbon solvents, since an aromatic group requires at least 6 carbon atoms and there would be 3 to 5 carbon atoms potentially forming an alkyl side group. The aromatic nature is expected to significantly alter the chemical properties including solubility of cannabinoids. Notwithstanding that aromatics are not preferred, there may be some aromatic content included in the solvent when a mixture of different molecules is present.

The $C_9$-$C_{11}$ non-aromatic hydrocarbon solvent may be a single molecule (mono-solvent) or a mixture of two or more molecules, such as 2, 3, 4, 5, 6, 7, 8, 9, or more distinct molecules. When there are multiple molecules, they may all be $C_9$, all $C_{10}$, all $C_{11}$, a mix of $C_9$ and $C_{10}$, a mix of $C_{10}$ or $C_{11}$, or a mix of $C_9$, $C_{10}$, and $C_{11}$.

The $C_9$-$C_{11}$ non-aromatic hydrocarbon solvent preferably has a purity of at least 90 wt %, at least 95 wt %, at least 99 wt %, or at least 99.9 wt %. Impurities in the $C_9$-$C_{11}$ non-aromatic hydrocarbon solvent may include water, dirt, salts, ash, and other hydrocarbons. When other hydrocarbons are present as impurities, those other hydrocarbons may be in a different class than $C_9$-$C_{11}$ non-aromatic hydrocarbons. For example, when a cyclic alkane (e.g., n-butylcyclohexane) is used in the solvent, there may be aromatic impurities (e.g., n-butylbenzene) arising from the original process to make the saturated cyclic hydrocarbon.

In some methods employing cooling crystallization of unreacted cannabinoids out of a $C_9$-$C_{11}$ non-aromatic hydrocarbon solvent, the first temperature is selected from about 20° C. to about 170° C., such as from about 30° C. to about 100° C. In this specification, ° C. is degrees Celsius, i.e. temperature or temperature difference on the Celsius scale. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges. In this specification, reference to "intervening ranges" is in reference to embodiments in which there is a sub-selection of conditions within a larger range of conditions. For instance, the first temperature may specifically be sub-selected within a range of 25-90° C., 30-150° C., or any other range that starts and ends with two of the recited temperatures.

In some methods employing cooling crystallization of unreacted cannabinoids out of a $C_9$-$C_{11}$ non-aromatic hydrocarbon solvent, the second temperature is selected from about −20° C. to about 150° C., such as from about −10° C. to about 100° C., or from about 0° C. to about 50° C. In various embodiments, the second temperature is about, at least about, or at most about −20° C., −15° C., −10° C., −5° C., 0° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., or 150° C., including all intervening ranges.

In some embodiments employing cooling crystallization of unreacted cannabinoids out of a $C_9$-$C_{11}$ non-aromatic hydrocarbon solvent, the temperature difference between the first temperature and the second temperature is from about 10° C. to about 200° C., such as from about 20° C. to about 100° C. In various embodiments, the temperature difference between the first temperature and the second temperature is about, at least about, or at most about 1° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., 170° C., 180° C., 190° C., or 200° C., including all intervening ranges.

The ratio of $C_9$-$C_{11}$ non-aromatic hydrocarbon solvent to cannabinoid-containing reaction mixture is typically selected based on the mass of unreacted cannabinoids (e.g., CBD) within the cannabinoid-containing reaction mixture. The mass ratio of solvent to unreacted cannabinoids may vary widely, such as from about 0.1 to about 10. In various embodiments, the mass ratio of solvent to unreacted cannabinoids is about, at least about, or at most about 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, 2, 2.5, 3, 3.5, 4, 5, 6, 7, 8, 9, or 10. Generally speaking, the lowest effective ratio of $C_9$-$C_{11}$ non-aromatic hydrocarbon solvent to unreacted cannabinoids should be employed to minimize heating, cooling, and recovery costs. The lowest effective ratio will depend on the crystallization conditions (e.g., temperature, pressure, and time). A person skilled in the chemical arts may conduct experiments to determine the optimal concentrations of solvent. Design of experiments, using statistical principles, may be employed to investigate the influence of changing concentrations as well as temperature, pressure, and time, including multi-factor interactions, for example.

The starting composition and the solvent may be separately introduced to the conversion reactor. Alternatively, or additionally, the starting composition and the solvent may be blended together and introduced to the conversion reactor.

Step (d) is preferably conducted at reaction conditions effective to chemically convert some, but not all, of the cannabinoid to a cannabinoid derivative, thereby generating a reaction mixture containing unreacted cannabinoid. In some embodiments, the cannabinoid conversion is selected from about 20% to about 80%, such as from about 30% to about 70%, or from about 40% to about 60%, for example. In certain embodiments, the cannabinoid conversion is no greater than 80%, or no greater than 70%, or no greater than 60%, or no greater than 50%.

The effective reaction conditions in step (d) may include a reaction temperature from about −20° C. to about 200° C., a reaction time from about 1 minute to about 120 hours, and/or a reaction pH from about 0.5 to about 12.

The chemical conversion of cannabinoid to cannabinoid derivative may involve solely molecular rearrangement (isomerization) with no elemental addition or retraction. In other embodiments, the chemical conversion of cannabinoid to cannabinoid derivative involves the addition of an element (e.g., hydrogen, carbon, oxygen, or a combination thereof). An example of chemical addition is hydrogenation with $H_2$. In other embodiments, the chemical conversion of cannabinoid to cannabinoid derivative involves the subtraction (elimination) of an element (e.g., carbon, oxygen, hydrogen, or a combination thereof). An example of chemical subtraction is decarboxylation releasing $CO_2$. Combinations of different types of chemical reactions may also occur, simultaneously or sequentially.

In some embodiments, the cannabinoid derivative is an isomer of the cannabinoid. In these embodiments, the effective reaction conditions may include the use of an isomerization catalyst (e.g., an enzyme).

In some embodiments, the effective reaction conditions include hydrogenation with hydrogen in the presence of a hydrogenation catalyst. The hydrogenation catalyst may be selected from the group consisting of platinum (Pt), palladium (Pd), rhodium (Rh), nickel (Ni), cobalt (Co), ruthenium (Ru), iridium (Ir), and combination thereof. In certain embodiments, the hydrogenation catalyst is platinum, palladium, nickel, or a combination thereof. Other metals may be employed, if they have at least some hydrogenation activity under the reaction conditions.

The hydrogenation catalyst is optionally disposed on a catalyst support. When the hydrogenation catalyst is disposed on a catalyst support, the catalyst support may be selected from the group consisting of activated carbon, alumina, silica, aluminosilicate, and combinations thereof. Other catalyst support media may be employed.

When hydrogenation is employed, the hydrogenation may convert a cannabinoid into a hydrogenated cannabinoid. Alternatively, or additionally, the hydrogenation may convert a cannabinoid derivative into a hydrogenated cannabinoid derivative. When the desired chemistry is to convert a cannabinoid into a cannabinoid derivative which in turn is converted into a hydrogenated cannabinoid derivative, all of these reaction steps may take place in a single conversion reactor. Alternatively, a first conversion reactor may be used for the step of converting a cannabinoid into a cannabinoid derivative, which is then fed to a second conversion reactor for converting the cannabinoid derivative into the hydrogenated cannabinoid derivative.

When hydrogenation is employed, a $C_9$-$C_{11}$ non-aromatic hydrocarbon such as n-decane may be used. Alternatively, a solvent other than a $C_9$-$C_{11}$ non-aromatic hydrocarbon may be used, which may improve the reaction kinetics. Polar solvents such as ketones (e.g., acetone), alcohols (e.g., methanol and/or ethanol) or mixtures thereof may be utilized. When different reactors are utilized for first converting a cannabinoid into a cannabinoid derivative, and then converting the cannabinoid derivative into the hydrogenated cannabinoid derivative (as discussed in the preceding paragraph), the conversion first reactor preferably utilizes a $C_9$-$C_{11}$ non-aromatic hydrocarbon solvent while the second conversion reactor need not utilize a $C_9$-$C_{11}$ non-aromatic hydrocarbon solvent.

In certain embodiments, the cannabinoid derivative is selected from D8-THC, D8-THCa, D8-iso-THC, D9-THC, D9-THCa, or a combination thereof, and the hydrogenated cannabinoid derivative is HHC. That HHC may be a racemic mixture of 9R-HHC and 9S-HHC. A ratio of the 9R-HHC to the 9S-HHC may be controlled by selecting the hydrogenation catalyst, the effective reaction conditions, and/or a ratio of (D8-THC+D8-THCa+D8-iso-THC) to (D9-THC+D9-THCa), which may be referred to as a D8-THC/D9-THC ratio.

In some embodiments, the process further comprises filtering and recycling the hydrogenation catalyst. The hydrogenation catalyst may be regenerated or reactivated prior to recycling, if needed.

High catalyst cost is a significant barrier for hydrogenation processes; therefore, an inexpensive and effective means of recovering catalyst is preferred. In some embodiments, a sub-micron filter is employed to capture the catalyst on a filter and then flush out the filtered catalyst material, to be reused.

Certain embodiments employ a settling technique in which the reaction chamber is taller than it is wide. This geometry allows the catalyst after a period of use to settle to the bottom of the reaction chamber. After settling is complete, a side draw may pull the reaction mixture out under laminar flow conditions. This technique allows two things. First, the hydrogenation catalyst is retained in the reaction chamber for ease of turn over. Second, the hydrogenation catalyst remains submerged under some liquid. It is important to handle the hydrogenation catalyst with care, because it can be flammable when hydrogen is adsorbed onto the surface. It is preferred that the hydrogenation catalyst not be allowed to dry out after a period of use, which will often mean there is adsorbed $H_2$.

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt (e.g., calcium acetate)

The effective reaction conditions in step (d) may include exposure to an acid catalyst, such as an aprotic Lewis acid. In some embodiments, an acid catalyst is selected from the group consisting of phosphoric acid, p-toluenesulfonic acid, citric acid, metal chlorides, metal bromides, metal fluorides, iodine-based acids, and combinations thereof. An exemplary acid catalyst is zinc bromide, which is an aprotic Lewis acid.

In certain embodiments, the acid catalyst is an aluminosilicate, which may be in the form of molecular sieves. These embodiments are premised on the surprising discovery that molecular sieves alone can be effective to catalyze the conversion of CBD to D9-THC, for example, without another catalytic material necessarily present. The molecular sieves may be of various sizes, such as (but not limited to) 3 Å, 4 Å, or 5 Å (Å=angstroms) as the average size of the pore opening. The selected size of the molecular sieves impacts the surface area of particles containing the molecular sieves, which in turn can have a significant impact on the chemical reaction kinetics. The molecules need to interact with the catalyst surface so the surface area can dramatically alter the mass-transfer limitations as well as the number of surface sites for catalysis to occur.

In some embodiments, the conversion reactor is a packed-bed reactor. The packed-bed reactor may contain a packing material comprising an acid catalyst. Alternatively, or additionally, the packed-bed reactor may contain a packing material comprising molecular sieves, such as to absorb water. When the packed-bed reactor contains a packing material comprising an acid catalyst as well as molecular sieves, the acid catalyst and the molecular sieves may be mixed together. Alternatively, the packed-bed reactor may contains a plurality of chamber, wherein at least a first chamber contains a first packing material comprising molecular sieves, and wherein at least a second chamber contains a second packing material comprising an acid catalyst (the second packing material optionally further comprises additional molecular sieves).

In some embodiments, the crystallization unit in step (f) is a Nutsche unit. The first temperature may be selected from about 20° C. to about 170° C., such as from about 30° C. to about 100° C., for example. The second temperature may be selected from about −20° C. to about 150° C., such as from about −10° C. to about 100° C., or from about 0° C. to about 50° C., for example. The temperature difference between the first temperature and the second temperature may from about 10° C. to about 200° C., such as from about 20° C. to about 100° C., as an measure of the degree of cooling of the reaction mixture in the crystallization unit.

In some embodiments, at least about 75%, 85%, 90%, or 95% of the unreacted cannabinoid is precipitated out of the reaction mixture. In various embodiments, at least about 50%, 55%, 60%, 65%, 70%, 75%, 80%, 85%, 90%, 95% or 99%, including all intervening ranges, of the unreacted cannabinoid is precipitated out of the reaction mixture.

In some embodiments, the cannabinoid derivative is recovered in a product that contains at least 50 vol % of the cannabinoid derivative. This means that the product composition is at least 50 vol % cannabinoid derivative. In some preferred embodiments, the cannabinoid derivative is recovered in a product that contains at least 75 vol %, or at least 90 vol %, of the cannabinoid derivative.

Step (g) may include separating the cannabinoid derivative from the mother liquor by utilizing a compressed gas, such as compressed air.

The process preferably further comprises recovering the solvent. The solvent may be recovered via vacuum extraction, for example. Some or all of the recovered solvent is preferably recycled back to step (b).

In some embodiments, the unreacted cannabinoid that is precipitated in step (f) is washed to remove residual cannabinoid derivative. Whether or not the unreacted and precipitated cannabinoid is washed, the precipitated cannabinoid from step (f) may be reused in step (a) as at least a portion of the starting composition.

In embodiments employing a Nutsche unit as the crystallization unit, the unreacted cannabinoid that is precipitated in step (f) may be recovered using a mesh screen disposed within the Nutsche unit. This configuration enables continuous or semi-continuous recovery of the precipitated cannabinoid.

In some embodiments, the process further comprises chromatographic purification of the cannabinoid derivative between step (f) and step (g), as part of step (g), or following step (g).

In various embodiments, step (g) or another process step utilizes evaporation, distillation, filtration, chromatography, membrane separation, or a combination thereof. One skilled in the art will recognize that these separation and purification unit operations may be used for various purposes, such as (but not limited to) increase in concentration of desired product (cannabinoid derivative), removal of impurities (e.g., color-causing impurities), removal of reaction byproducts (e.g., cannabinoid decomposition products or unwanted tertiary products), removal of residual solvent, removal of water, removal of particulates, and so on.

The cannabinoid derivative may be selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof (e.g., HHC, hexahydrocannabinol), acetylated variants thereof (e.g., D8-THC-O-acetate), and combinations of the foregoing.

In certain embodiments, the cannabinoid derivative includes D9-THC or consists essentially of D9-THC.

In certain embodiments, the cannabinoid derivative includes D8-iso-THC. It is believed, without limitation, that D8-iso-THC is a reaction byproduct that may be created during the conversion of CBD into D9-THC. D8-iso-THC itself is believed to exist as different stereoisomers, and it may be present as a racemic mixture.

There may be a single cannabinoid derivative or multiple cannabinoid derivatives that are produced by the disclosed processes. Also, there may be various reaction intermediates, such as CBDa (cannabidiolic acid) produced from CBD, which CBDa is, in turn, converted to one or more other cannabinoid derivatives. Generally speaking, there may be a reaction network with a plurality of reactants, reaction intermediates, and products (cannabinoid derivatives) with an intermediate or final product distribution dictated by reaction kinetics, chemical equilibrium, mass-transfer rates, or a combination thereof.

The process is preferably continuous or semi-continuous. In some embodiments, some, but not all, steps are continuous or semi-continuous. For example, steps (d), (e), and (f) may be continuous while other steps are in batch or semi-batch mode. In certain embodiments, the entire process is conducted in batch or semi-batch mode.

The present invention also provides a cannabinoid derivative product produced by a process as disclosed. In some embodiments, a cannabinoid derivative product consists essentially of D9-THC, substantially free of side products and catalyst contamination. In certain embodiments, a cannabinoid derivative product consists essentially of D9-THC and CBD (product and reactant, respectively), substantially free of side products and catalyst contamination.

The cannabinoid derivative product may be in liquid form along with an edible oil, such as vegetable oil (e.g., olive oil), and/or other conventional additives that do not materially affect the function of D9-THC (or other cannabinoid derivative). The cannabinoid derivative product may be in solid (e.g., powder) form. The cannabinoid derivative product may be in the form of various consumer products, such as gummies, candies, lotions, and the like.

Other variations of the invention provide a system for converting a cannabinoid into a purified cannabinoid derivative, the system comprising:

a conversion reactor configured with at least one inlet for a starting composition comprising a cannabinoid as well as a solvent comprising a $C_9$-$C_{11}$ non-aromatic hydrocarbon, wherein the conversion reactor is configured to chemically convert some, but not all, of the cannabinoid to a cannabinoid derivative at a cannabinoid conversion, thereby generating a reaction mixture containing unreacted cannabinoid;

a crystallization unit in flow communication with the conversion reactor, wherein the crystallization unit is configured to cool the reaction mixture to precipitate unreacted cannabinoid out of the reaction mixture, thereby generating a mother liquor containing the cannabinoid derivative;

a solvent recovery unit in flow communication with the crystallization unit, wherein the solvent recovery unit is configured to remove the solvent from the mother liquor to generate a purified cannabinoid derivative; and one or more heat exchangers configured to heat and/or cool the conversion reactor, the crystallization unit, and/or the solvent recovery unit.

FIG. 1 is an exemplary block-flow diagram of a process and system for converting a cannabinoid into a purified cannabinoid derivative, in some embodiments. The diagram of FIG. 1 includes a conversion reactor, a crystallization unit, and a solvent recovery unit. Unreacted cannabinoid from the crystallization unit may be recycled to the conversion reactor. Recovered solvent from the solvent recovery unit may also be recycled to the conversion reactor. In all drawings herein, dotted lines denote optional streams and units. In FIG. 1, there are optional heat exchangers to heat and/or cool other units, i.e., the conversion reactor, the crystallization unit, and the solvent recovery unit. The heat flows to and from the units, from the heat exchangers, are not shown. In some embodiments, a unit is configured for direct heating or cooling, such as via a heating or cooling jacket, rather than a physically separated heat exchanger.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include n-decane, or consist essentially of n-decane, for example.

The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne.

In some systems, the conversion reactor is a packed-bed reactor. The packed-bed reactor may contain a packing material comprising an acid catalyst, such as an aprotic Lewis acid (e.g., zinc bromide). In various systems, the acid catalyst is selected from the group consisting of phosphoric acid, p-toluenesulfonic acid, citric acid, metal chlorides, metal bromides, metal fluorides, iodine-based acids, and combinations thereof.

The packed-bed reactor (if present) may contains a packing material comprising molecular sieves. In some embodiments, a packed-bed reactor contains a packing material comprising an acid catalyst as well as molecular sieves, wherein the acid catalyst and the molecular sieves are optionally mixed together. In certain embodiments, the packed-bed reactor contains a plurality of chambers, wherein at least a first chamber contains a first packing material comprising molecular sieves, and wherein at least a second chamber contains a second packing material comprising an acid catalyst and possibly additional molecular sieves.

In some systems, the crystallization unit is a Nutsche unit. A Nutsche unit may include a mesh screen configured for recovering precipitated, unreacted cannabinoid.

In some systems, the solvent recovery unit is configured to recover the solvent using a compressed gas, such as compressed air. The solvent recovery unit may be a vacuum extraction unit.

The system may further include a chromatographic purification unit configured to purify the cannabinoid derivative. The chromatographic purification unit may be disposed between the crystallization unit and the solvent recovery unit. Alternatively, the chromatographic purification unit may be disposed between the solvent recovery unit and a product storage tank or container.

In various system embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In various system embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof. In particular embodiments, the cannabinoid derivative includes D9-THC or consists essentially of D9-THC.

The system is preferably configured to operate continuously or semi-continuously. The system is preferably automated using a programmable logic controller.

Other variations of the invention provide a process of converting a terpene into a purified terpene derivative, the process comprising:
(a) providing a starting composition comprising a terpene;
(b) providing a solvent comprising a $C_9$-$C_{11}$ non-aromatic hydrocarbon;
(c) introducing the starting composition and the solvent to a conversion reactor;
(d) operating the conversion reactor at effective reaction conditions to chemically convert the terpene to a terpene derivative at a terpene conversion selected from about 10% to about 90%, thereby generating a reaction mixture containing unreacted terpene;
(e) conveying the reaction mixture to a crystallization unit;
(f) within the crystallization unit, cooling the reaction mixture from a first temperature to a second temperature that is lower than the first temperature, to precipitate at least about 50% of the unreacted terpene out of the reaction mixture, thereby generating a mother liquor containing the terpene derivative; and
(g) isolating and recovering the terpene derivative from the mother liquor.

In some embodiments, the terpene is selected from the group consisting of α-pinene, β-pinene, β-thujone, 3-carene, terpinolene, limonene, terpineol, 1,8-cineole, α-terpinene, linalool, myrcene, β-ocimene, α-elemol, β-farnesol, β-farnesene, bisabolol, α-bergamotene, δ-cadinene, γ-eudesmol, valencene, eremophilene, β-himachalene, α-guaiene, germacrene, alloaromadendrene, β-caryophyllene, α-humulene, ocimene, δ-selinene, and combinations thereof.

The starting composition may be obtained from exposing a starting terpene-containing plant material to a process solvent, such as supercritical carbon dioxide. In some embodiments, the process solvent is not a $C_9$-$C_{11}$ non-aromatic hydrocarbon or is not n-decane. The process solvent may be a hydrocarbon, such as a $C_2$-$C_8$ alkane. The process solvent may be a $C_1$-$C_{12}$ alcohol, such as ethanol.

Alternatively, or additionally, the starting composition may be obtained from a chemical reaction of a starting terpene-containing plant material, or a starting external source, prior to and separate from step (d), i.e., in a chemical conversion that takes place prior to step (a). A starting terpene-containing plant material may be selected from *Cannabis sativa, Cannabis indica, Cannabis ruderalis,*

*Echinacea purpurea, Echinacea angustifolia, Acmella oleracea, Helichrysum umbraculigerum*, or *Radula marginata*.

In some embodiments related to terpenes, the starting composition is characterized by a terpene concentration of at least about 50 vol %, wherein the terpene concentration is calculated as mass of the terpene divided by mass of all terpenes contained in the starting composition.

In some embodiments, during step (c), a terpene/solvent ratio is selected from about 0.5 to about 2.0, calculated as volume of the terpene divided by volume of the $C_9$-$C_{11}$ non-aromatic hydrocarbon solvent. The terpene/solvent ratio may be selected from about 0.7 to about 1.3, such as about 0.8 to about 1.2, for example.

In some processes related to terpenes, the $C_9$-$C_{11}$ non-aromatic hydrocarbon is a $C_{10}$ linear, cyclic, or branched alkane, alkene, or alkyne. In certain embodiments, the $C_9$-$C_{11}$ non-aromatic hydrocarbon includes n-decane, or consists essentially of n-decane. The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne. Combinations of $C_9$-$C_{11}$ non-aromatic hydrocarbons may be utilized in the solvent.

The $C_9$-$C_{11}$ non-aromatic hydrocarbon is a crystallization-inducing solvent, for terpenes as in the case of cannabinoids. Generally, $C_9$-$C_{11}$ non-aromatic hydrocarbons may be alkanes (only single C—C bonds present), alkenes (one or more C=C double bonds present), or alkynes (one or more C≡C triple bonds present) and may be linear, cyclic, or branched.

In some embodiments related to terpenes, the solvent is a $C_{10}$ non-aromatic hydrocarbon solvent. Especially preferred are $C_{10}$ alkanes, which are decane and any of its isomers. That is, in preferred embodiments, the solvent is selected from the group consisting of n-decane, 2-methylnonane, 3-methylnonane, 4-methylnonane, 5-methylnonane, 3-ethyloctane, 4-ethyloctane, 2,2-dimethyloctane, 2,3-dimethyloctane, 2,4-dimethyloctane, 2,5-dimethyloctane, 2,6-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, 4-propylheptane, 4-isopropylheptane, 2-methyl-3-ethylheptane, 2-methyl-4-ethylheptane, 2-methyl-5-ethylheptane, 3-methyl-3-ethylheptane, 3-methyl-4-ethylheptane, 3-methyl-5-ethylheptane, 4-methyl-3-ethylheptane, 4-methyl-4-ethylheptane, 2,2,3-trimethylheptane, 2,2,4-trimethylheptane, 2,2,5-trimethylheptane, 2,2,6-trimethylheptane, 2,3,3-trimethylheptane, 2,3,4-trimethylheptane, 2,3,5-trimethylheptane, 2,3,6-trimethylheptane, 2,4,4-trimethylheptane, 2,4,5-trimethylheptane, 2,4,6-trimethylheptane, 2,5,5-trimethylheptane, 3,3,4-trimethylheptane, 3,3,5-trimethylheptane, 3,4,4-trimethylheptane, 3,4,5-trimethylheptane, 2-methyl-3-isopropylhexane, 3,3-diethylhexane, 3,4-diethylhexane, 2,2-dimethyl ethylhexane, 2,2-dimethyl-4-ethylhexane, 2,3-dimethyl-3-ethylhexane, 2,3-dimethyl ethylhexane, 2,4-dimethyl-3-ethylhexane, 2,4-dimethyl-4-ethylhexane, 2,5-dimethyl ethylhexane, 3,3-dimethyl-4-ethylhexane, 3,4-dimethyl-3-ethylhexane, 2,2,3,3-tetramethylhexane, 2,2,3,4-tetramethylhexane, 2,2,3,5-tetramethylhexane, 2,2,4,4-tetramethylhexane, 2,2,4,5-tetramethylhexane, 2,2,5,5-tetramethylhexane, 2,3,3,4-tetramethylhexane, 2,3,3,5-tetramethylhexane, 2,3,4,4-tetramethylhexane, 2,3,4,5-tetramethylhexane, 3,3,4,4-tetramethylhexane, 2,4-dimethyl-3-isopropylpentane, 2-methyl-3,3-diethylpentane, 2,2,3-trimethyl-3-ethylpentane, 2,2,4-trimethyl-3-ethylpentane, 2,3,4-trimethyl-3-ethylpentane, 2,2,3,3,4-pentamethylpentane, 2,2,3,4,4-pentamethylpentane, and combinations thereof. In certain preferred embodiments, the solvent is specifically n-decane, n-$C_{10}H_{22}$, or is a solvent comprising n-decane.

In some embodiments, the $C_9$-$C_{11}$ non-aromatic hydrocarbon solvent is a $C_{10}$ linear, cyclic, or branched alkane solvent. Linear or branched $C_{10}$ alkanes generally have the formula $C_{10}H_{22}$, while cyclic $C_{10}$ alkanes have less hydrogen (e.g., cyclodecane is $C_{10}H_{20}$).

In some embodiments, the $C_9$-$C_{11}$ non-aromatic hydrocarbon solvent is a $C_{10}$ linear, cyclic, or branched alkene solvent. An alkene contains at least one carbon-carbon double bond, C=C. Exemplary $C_{10}$ alkenes are 1-decene or 4-decene, for instance. Linear or branched $C_{10}$ single alkenes generally have the formula $C_{10}H_{20}$, while cyclic $C_{10}$ alkenes have less hydrogen.

In some embodiments, the $C_9$-$C_{11}$ non-aromatic hydrocarbon solvent is a $C_{10}$ linear, cyclic, or branched alkyne solvent. An alkyne contains at least one carbon-carbon triple bond, Exemplary $C_{10}$ alkynes are 1-decyne and 2-decyne, for instance. Linear or branched $C_{10}$ single alkynes generally have the formula $C_{10}H_{18}$, while cyclic $C_{10}$ alkynes have less hydrogen.

In some embodiments, the $C_9$-$C_{11}$ non-aromatic hydrocarbon solvent is a $C_9$ linear, cyclic, or branched alkane solvent, a $C_9$ linear, cyclic, or branched alkene solvent, a $C_9$ linear, cyclic, or branched alkyne solvent, or a combination thereof. Examples of $C_9$ solvents include n-nonane, 1-nonene, 1-nonyne, and bicyclo[3.3.1]nonane. Linear and branched $C_9$ alkanes generally have the formula $C_9H_{20}$, linear and branched $C_9$ single alkenes generally have the formula $C_9H_{18}$, and linear and branched $C_9$ single alkynes generally have the formula $C_9H_{16}$.

In some embodiments, the $C_9$-$C_{11}$ non-aromatic hydrocarbon solvent is a $C_{11}$ linear, cyclic, or branched alkane solvent, a $C_{11}$ linear, cyclic, or branched alkene solvent, a $C_{11}$ linear, cyclic, or branched alkyne solvent, or a combination thereof. Examples of $C_{11}$ solvents include n-undecane, 5-undecene, and 3-undecyne. Linear and branched $C_{11}$ alkanes generally have the formula $C_{11}H_{24}$, linear and branched $C_{11}$ single alkenes generally have the formula $C_{11}H_{22}$, and linear and branched $C_{11}$ single alkynes generally have the formula $C_{11}H_{20}$. Examples of $C_{11}$ bicyclo solvents include bicyclo[6.1.1]decane, $C_{10}H_{18}$ and 2-methylbicyclo[4.2.2]decane, $C_{11}H_{20}$.

$C_9$ to $C_{11}$ aromatic hydrocarbon solvents (e.g., n-butylbenzene, $C_{10}H_{14}$) are not expected to work as well as $C_9$ to $C_{11}$ non-aromatic hydrocarbon solvents, since an aromatic group requires at least 6 carbon atoms and there would be 3 to 5 carbon atoms potentially forming an alkyl side group. The aromatic nature is expected to significantly alter the chemical properties including solubility of terpenes. Notwithstanding that aromatics are not preferred, there may be some aromatic content included in the solvent when a mixture of different molecules is present.

The $C_9$-$C_{11}$ non-aromatic hydrocarbon solvent may be a single molecule (mono-solvent) or a mixture of two or more molecules, such as 2, 3, 4, 5, 6, 7, 8, 9, or more distinct molecules. When there are multiple molecules, they may all be $C_9$, all $C_{10}$, all $C_{11}$, a mix of $C_9$ and $C_{10}$, a mix of $C_{10}$ or $C_{11}$, or a mix of $C_9$, $C_{10}$, and $C_{11}$.

The $C_9$-$C_{11}$ non-aromatic hydrocarbon solvent preferably has a purity of at least 90 wt %, at least 95 wt %, at least 99 wt %, or at least 99.9 wt %. Impurities in the $C_9$-$C_{11}$ non-aromatic hydrocarbon solvent may include water, dirt, salts, ash, and other hydrocarbons. When other hydrocarbons are present as impurities, those other hydrocarbons may be in a different class than $C_9$-$C_{11}$ non-aromatic hydrocarbons. For example, when a cyclic alkane (e.g., n-butylcyclohexane) is used in the solvent, there may be aromatic impurities (e.g., n-butylbenzene) arising from the original process to make the saturated cyclic hydrocarbon.

In some methods employing cooling crystallization of unreacted terpenes out of a $C_9$-$C_{11}$ non-aromatic hydrocarbon solvent, the first temperature is selected from about 20° C. to about 170° C., such as from about 30° C. to about 100° C. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges.

In some methods employing cooling crystallization of unreacted terpenes out of a $C_9$-$C_{11}$ non-aromatic hydrocarbon solvent, the second temperature is selected from about −20° C. to about 150° C., such as from about −10° C. to about 100° C., or from about 0° C. to about 50° C. In various embodiments, the second temperature is about, at least about, or at most about −20° C., −15° C., −10° C., −5° C., 0° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., or 150° C., including all intervening ranges.

In some embodiments employing cooling crystallization of unreacted terpenes out of a $C_9$-$C_{11}$ non-aromatic hydrocarbon solvent, the temperature difference between the first temperature and the second temperature is from about 10° C. to about 200° C., such as from about 20° C. to about 100° C. In various embodiments, the temperature difference between the first temperature and the second temperature is about, at least about, or at most about 1° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., 170° C., 180° C., 190° C., or 200° C., including all intervening ranges.

The ratio of $C_9$-$C_{11}$ non-aromatic hydrocarbon solvent to terpene-containing reaction mixture is typically selected based on the mass of unreacted terpenes (e.g., α-pinene) within the terpene-containing reaction mixture. The mass ratio of solvent to unreacted terpenes may vary widely, such as from about 0.1 to about 10. In various embodiments, the mass ratio of solvent to unreacted terpenes is about, at least about, or at most about 0.1, 0.2, 0.3, 5, 6, 7, 8, 9, or 10. Generally speaking, the lowest effective ratio of $C_9$-$C_{11}$ non-aromatic hydrocarbon solvent to unreacted terpenes should be employed to minimize heating, cooling, and recovery costs. The lowest effective ratio will depend on the crystallization conditions (e.g., temperature, pressure, and time). A person skilled in the chemical arts may conduct experiments to determine the optimal concentrations of solvent. Design of experiments, using statistical principles, may be employed to investigate the influence of changing concentrations as well as temperature, pressure, and time, including multi-factor interactions, for example.

The starting composition and the solvent may be separately introduced to the conversion reactor. Alternatively, or additionally, the starting composition and the solvent may be blended together and introduced to the conversion reactor.

Step (d) is preferably conducted at reaction conditions effective to chemically convert some, but not all, of the terpene to a terpene derivative, thereby generating a reaction mixture containing unreacted terpene. In some embodiments, the terpene conversion is selected from about 20% to about 80%, such as from about 30% to about 70%, or from about 40% to about 60%, for example. In certain embodiments, the terpene conversion is no greater than 80%, or no greater than 70%, or no greater than 60%, or no greater than 50%.

In processes relating to terpenes, the effective reaction conditions in step (d) may include a reaction temperature from about −20° C. to about 200° C., a reaction time from about 1 minute to about 120 hours, and/or a reaction pH from about 0.5 to about 12.

In some embodiments relating to terpenes, the terpene derivative is an isomer of the terpene.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. The optional catalyst support may be selected from the group consisting of activated carbon, alumina, silica, aluminosilicate, and combinations thereof. The hydrogenation catalyst may be filtered and recycled.

In some embodiments, hydrogenation converts a terpene into a hydrogenated terpene. In these or other embodiments, hydrogenation converts a terpene derivative into a hydrogenated terpene derivative.

In some embodiments, the effective reaction conditions include acetylation of the terpene with acetic acid or an acetate salt. In these or other embodiments, the effective reaction conditions include acetylation of the terpene derivative with acetic acid or an acetate salt.

The effective reaction conditions in step (d) may include exposure to an acid catalyst, such as an aprotic Lewis acid. In some embodiments, an acid catalyst is selected from the group consisting of phosphoric acid, p-toluenesulfonic acid, citric acid, metal chlorides, metal bromides, metal fluorides, iodine-based acids, and combinations thereof. An exemplary acid catalyst is zinc bromide, which is an aprotic Lewis acid.

In some embodiments related to terpenes, the conversion reactor is a packed-bed reactor. The packed-bed reactor may contain a packing material comprising an acid catalyst. Alternatively, or additionally, the packed-bed reactor may contain a packing material comprising molecular sieves, such as to absorb water. When the packed-bed reactor contains a packing material comprising an acid catalyst as well as molecular sieves, the acid catalyst and the molecular sieves may be mixed together. Alternatively, the packed-bed reactor may contains a plurality of chamber, wherein at least a first chamber contains a first packing material comprising molecular sieves, and wherein at least a second chamber contains a second packing material comprising an acid catalyst (the second packing material optionally further comprises additional molecular sieves).

In some embodiments related to terpenes, the crystallization unit in step (f) is a Nutsche unit. The first temperature may be selected from about 20° C. to about 170° C., such as from about 30° C. to about 100° C., for example. The second temperature may be selected from about −20° C. to about 150° C., such as from about −10° C. to about 100° C., or from about 0° C. to about 50° C., for example. The temperature difference between the first temperature and the second temperature may from about 10° C. to about 200° C., such as from about 20° C. to about 100° C., as an measure of the degree of cooling of the reaction mixture in the crystallization unit.

In some embodiments, at least about 75%, 85%, 90%, or 95% of the unreacted terpene is precipitated out of the reaction mixture. In various embodiments, at least about 50%, 55%, 60%, 65%, 70%, 75%, 80%, 85%, 90%, 95% or 99%, including all intervening ranges, of the unreacted terpene is precipitated out of the reaction mixture.

In some embodiments, the terpene derivative is recovered in a product that contains at least 50 vol % of the terpene derivative. This means that the product composition is at least 50 vol % terpene derivative. In some preferred embodiments, the terpene derivative is recovered in a product that contains at least 75 vol %, or at least 90 vol %, of the terpene derivative.

Step (g) may include separating the terpene derivative from the mother liquor by utilizing a compressed gas, such as compressed air.

The process preferably further comprises recovering the solvent. The solvent may be recovered via vacuum extraction, for example. Some or all of the recovered solvent is preferably recycled back to step (b).

In some embodiments, the unreacted terpene that is precipitated in step (f) is washed to remove residual terpene derivative. Whether or not the unreacted and precipitated terpene is washed, the precipitated terpene from step (f) may be reused in step (a) as at least a portion of the starting composition.

In embodiments employing a Nutsche unit as the terpene crystallization unit, the unreacted terpene that is precipitated in step (f) may be recovered using a mesh screen disposed within the Nutsche unit. This configuration enables continuous or semi-continuous recovery of the precipitated terpene.

In some embodiments, the process further comprises chromatographic purification of the terpene derivative between step (f) and step (g), as part of step (g), or following step (g).

The terpene derivative may be a cannabinoid selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

The terpene derivative may be selected from the group consisting of CBD, CBDa, CBG, CBGa, D6-THC, D6-THCa, D8-THC, D8-THCa, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof.

In certain embodiments, the terpene derivative includes D9-THC or consists essentially of D9-THC.

There may be a single terpene derivative or multiple terpene derivatives that are produced by the disclosed processes. Also, there may be various reaction intermediates which are then converted to one or more other terpene derivatives. Generally speaking, there may be a reaction network with a plurality of reactants, reaction intermediates, and products (terpene derivatives) with an intermediate or final product distribution dictated by reaction kinetics, chemical equilibrium, mass-transfer rates, or a combination thereof.

The process is preferably continuous or semi-continuous. In some embodiments, some, but not all, steps are continuous or semi-continuous. For example, steps (d), (e), and (f) may be continuous while other steps are in batch or semi-batch mode. In certain embodiments, the entire process is conducted in batch or semi-batch mode.

The present invention also provides a terpene derivative product produced by a process as disclosed. In some embodiments, a terpene derivative product consists essentially of D9-THC, substantially free of side products and catalyst contamination.

The terpene derivative product may be in liquid form along with an edible oil, such as vegetable oil (e.g., olive oil), and/or other conventional additives that do not materially affect the terpene-derivative function. The terpene derivative product may be in solid (e.g., powder) form. The terpene derivative product may be in the form of various consumer products, such as gummies, candies, lotions, and the like.

Still other variations of the invention provide a system for converting a terpene into a purified terpene derivative, the system comprising:

a conversion reactor configured with at least one inlet for a starting composition comprising a terpene as well as a solvent comprising a $C_9$-$C_{11}$ non-aromatic hydrocarbon, wherein the conversion reactor is configured to chemically convert some, but not all, of the terpene to a terpene derivative at a terpene conversion, thereby generating a reaction mixture containing unreacted terpene;

a crystallization unit in flow communication with the conversion reactor, wherein the crystallization unit is configured to cool the reaction mixture to precipitate unreacted terpene out of the reaction mixture, thereby generating a mother liquor containing the terpene derivative;

a solvent recovery unit in flow communication with the crystallization unit, wherein the solvent recovery unit is configured to remove the solvent from the mother liquor to generate a purified terpene derivative; and one or more heat exchangers configured to heat and/or cool the conversion reactor, the crystallization unit, and/or the solvent recovery unit.

Figure 2:
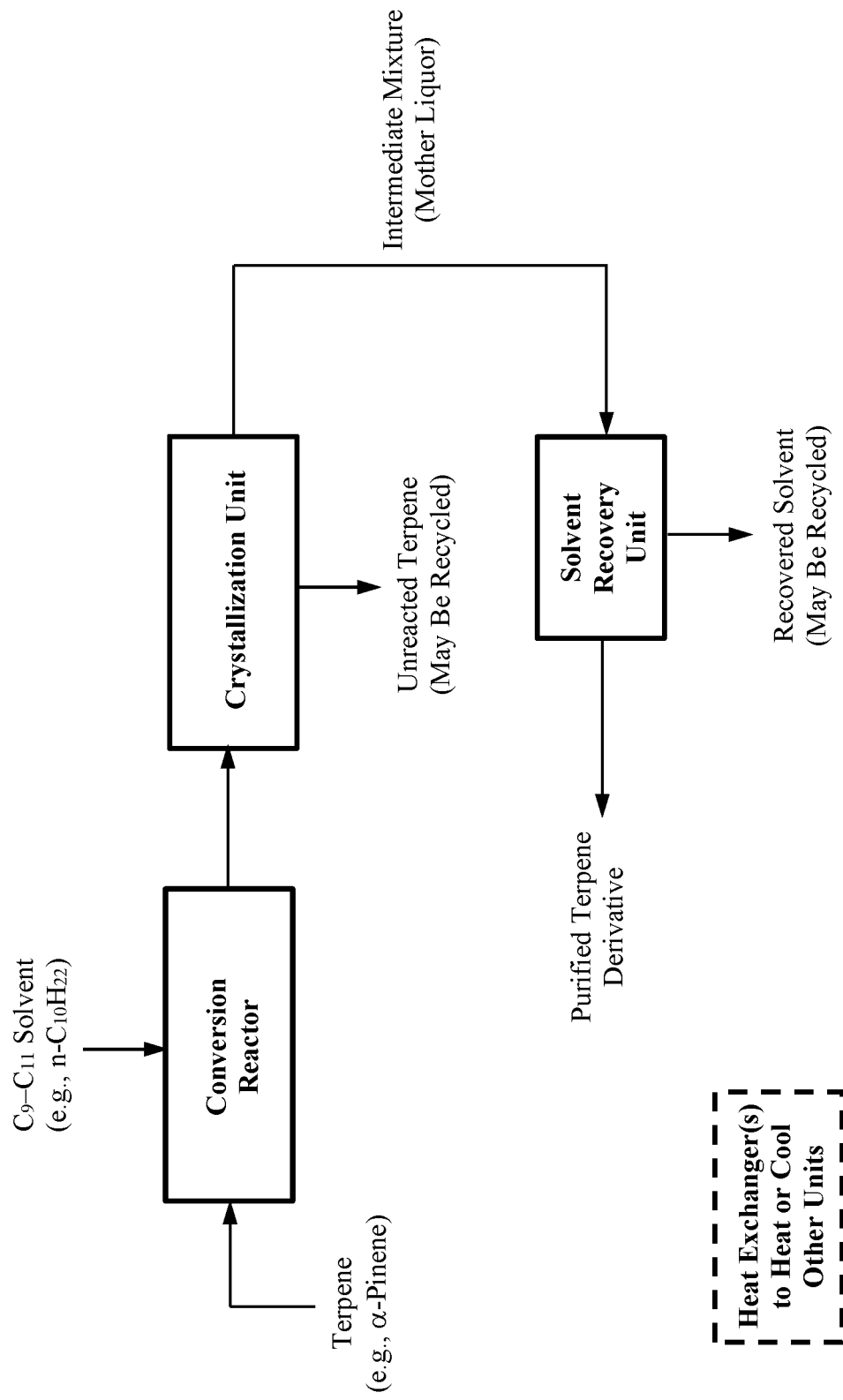
FIG. 2 is an exemplary block-flow diagram of a process and system for converting a terpene into a purified terpene derivative, in some embodiments.

FIG. 2 is an exemplary block-flow diagram of a process and system for converting a terpene into a purified terpene derivative, in some embodiments. The diagram of FIG. 2 includes a conversion reactor, a crystallization unit, and a solvent recovery unit. Unreacted terpene from the crystallization unit may be recycled to the conversion reactor. Recovered solvent from the solvent recovery unit may also be recycled to the conversion reactor. In FIG. 2, there are optional heat exchangers to heat and/or cool other units, i.e., the conversion reactor, the crystallization unit, and the solvent recovery unit. The heat flows to and from the units, from the heat exchangers, are not shown. In some embodiments, a unit is configured for direct heating or cooling, such as via a heating or cooling jacket, rather than a physically separated heat exchanger.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include n-decane, or consist essentially of n-decane, for example.

The $C_9$-$C_{11}$ non-aromatic hydrocarbon may be a $C_9$ linear, cyclic, or branched alkane, alkene, or alkyne. The $C_9$-$C_{11}$ non-aromatic hydrocarbon may be a $C_{11}$ linear, cyclic, or branched alkane, alkene, or alkyne.

In some systems relating to terpenes, the conversion reactor is a packed-bed reactor. The packed-bed reactor may contain a packing material comprising an acid catalyst, such as an aprotic Lewis acid (e.g., zinc bromide). In various systems, the acid catalyst is selected from the group consisting of phosphoric acid, p-toluenesulfonic acid, citric acid, metal chlorides, metal bromides, metal fluorides, iodine-based acids, and combinations thereof.

The packed-bed reactor (if present) may contains a packing material comprising molecular sieves. In some embodiments, a packed-bed reactor contains a packing material comprising an acid catalyst as well as molecular sieves, wherein the acid catalyst and the molecular sieves are optionally mixed together. In certain embodiments, the packed-bed reactor contains a plurality of chambers, wherein at least a first chamber contains a first packing material comprising molecular sieves, and wherein at least a second chamber contains a second packing material comprising an acid catalyst and possibly additional molecular sieves.

In some systems, the terpene crystallization unit is a Nutsche unit. A Nutsche unit may include a mesh screen configured for recovering precipitated, unreacted terpene.

In some systems, the solvent recovery unit is configured to recover the solvent using a compressed gas, such as compressed air. The solvent recovery unit may be a vacuum extraction unit.

The system may further include a chromatographic purification unit configured to purify the terpene derivative. The chromatographic purification unit may be disposed between the crystallization unit and the solvent recovery unit. Alternatively, the chromatographic purification unit may be disposed between the solvent recovery unit and a product storage tank or container.

In various system embodiments, the terpene is selected from the group consisting of α-pinene, β-pinene, β-thujone, 3-carene, terpinolene, limonene, terpineol, 1,8-cineole, α-terpinene, linalool, myrcene, β-ocimene, α-elemol, β-farnesol, β-farnesene, bisabolol, α-bergamotene, δ-cadinene, γ-eudesmol, valencene, eremophilene, β-himachalene, α-guaiene, germacrene, alloaromadendrene, β-caryophyllene, α-humulene, ocimene, δ-selinene, and combinations thereof.

In various system embodiments, the terpene derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, HHC, and combinations thereof. In particular embodiments, the terpene derivative includes D9-THC or consists essentially of D9-THC.

The system is preferably configured to operate continuously or semi-continuously. Known chemical-engineering principles may be applied to design a continuous or semi-continuous system, including heat exchangers for heating and cooling, containers for intermediate or final storage, pumps, valves, pipes or tubing, and so on.

The system is preferably automated using a programmable logic controller. Automation is beneficial to monitor and control process conditions for reaction and precipitation, flow rates, and recycle streams, for example. Programmable logic control (PLC) is well-known in modern process industries. Standard safety controls are preferably included in the system.

Any of the systems disclosed herein may be configured to be modular or portable, if desired.

The throughput of a system may vary widely, from small demo or semi-commercial scale to large commercial scale. The designs disclosed herein can be adapted using known chemical-engineering principles to any scale system for production of large, commercial volumes of products.

The selection of the materials of construction for the system will be dependent on the desired properties and should be considered on a case-by-case basis. Someone skilled in the art of material science or metallurgy will be able to select the appropriate materials for the intended use, based on the information provided in this disclosure.

Other variations provide a process of converting a cannabinoid into a cannabinoid derivative utilizing a high-temperature conversion reactor, the process comprising:

(a) providing a starting composition comprising a cannabinoid;

(b) providing a solvent comprising a $C_9$-$C_{11}$ non-aromatic hydrocarbon;

(c) introducing the starting composition and the solvent to a conversion reactor;

(d) operating the conversion reactor at effective reaction conditions to chemically convert the cannabinoid to a cannabinoid derivative at a cannabinoid conversion selected from about 10% to about 100%, thereby generating a reaction mixture, wherein the effective reaction conditions include a reaction temperature selected from about 100° C. to about 170° C.; and (e) recovering the cannabinoid derivative from the reaction mixture.

Figure 3:
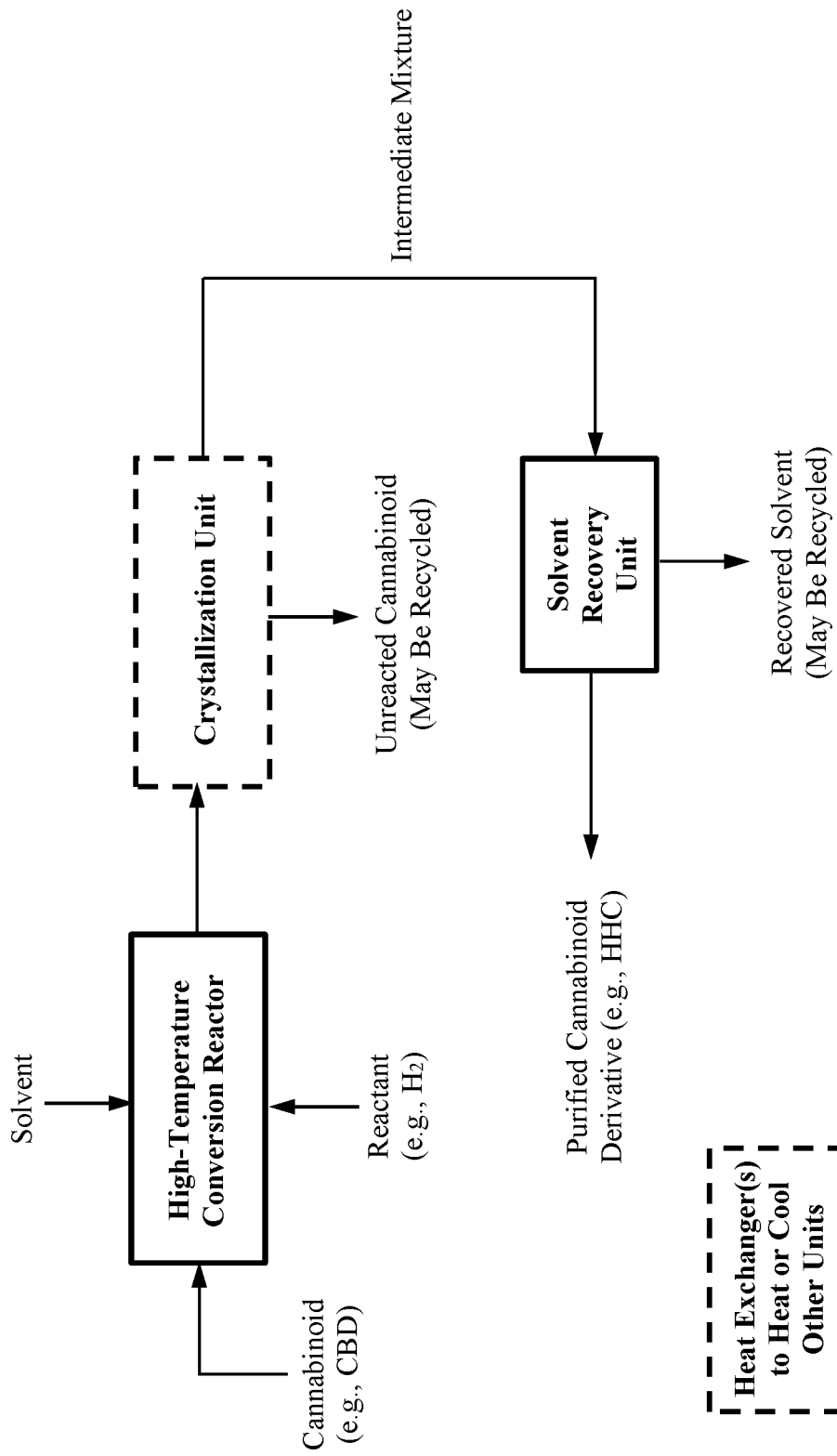
FIG. 3 is an exemplary block-flow diagram of a process and system for converting a cannabinoid into a purified cannabinoid derivative, in some embodiments.

FIG. 3 is an exemplary block-flow diagram of a process and system for converting a cannabinoid into a purified cannabinoid derivative, in some embodiments.

In some embodiments, the cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In certain embodiments, the cannabinoid is cannabidiol. In certain embodiments, the cannabinoid is cannabigerol.

In some embodiments, the starting composition is characterized by a cannabinoid purity of at least about 75 vol % or at least about 90 vol %, wherein the cannabinoid purity is calculated as mass of the cannabinoid divided by mass of all cannabinoids contained in the starting composition.

In some embodiments, during step (c), a cannabinoid/solvent ratio is selected from about 0.5 to about 2.0, calculated as volume of the cannabinoid divided by volume of the $C_9$-$C_{11}$ non-aromatic hydrocarbon solvent. The cannabinoid/solvent ratio may be selected from about 0.8 to about 1.2, for example.

In some embodiments, the $C_9$-$C_{11}$ non-aromatic hydrocarbon is a $C_{10}$ linear, cyclic, or branched alkane, alkene, or alkyne. In certain embodiments, the $C_9$-$C_{11}$ non-aromatic hydrocarbon includes n-decane.

In some embodiments, the $C_9$-$C_{11}$ non-aromatic hydrocarbon is a $C_9$ linear, cyclic, or branched alkane, alkene, or alkyne.

In some embodiments, the $C_9$-$C_{11}$ non-aromatic hydrocarbon is a $C_{11}$ linear, cyclic, or branched alkane, alkene, or alkyne.

In some embodiments, the starting composition and the solvent are blended together and introduced to the conversion reactor.

A reaction temperature from about 100° C. to about 170° C. is a high temperature that benefits from the selection of $C_9$-$C_{11}$ non-aromatic hydrocarbon solvents, such as n-decane. The present inventor has shown that n-decane is surprisingly useful in high-temperature (100-170° C.) cannabinoid reactions. Unless the reaction is performed in a pressurized vessel, the reactor contents cannot reach a higher temperature than the solvent boiling point, due to the latent heat of the solvent, unless all solvent is driven off which is undesirable. The normal (1 bar) boiling point of n-decane is 174° C. Because n-decane has a relatively low vapor pressure at temperatures of about 100-130° C., performing reactions in this temperature range is preferred in some embodiments as being easier and safer.

In some embodiments, the reaction temperature is selected from about 100° C. to about 130° C., or from about 130° C. to about 170° C. In various embodiments, the reaction temperature is about, at least about, or at most about 100° C., 105° C., 110° C., 115° C., 120° C., 125° C., 130° C., 135° C., 140° C., 145° C., 150° C., 155° C., 160° C., 165° C., or 170° C., including any intervening ranges. In some embodiments, the reaction temperature is selected to be below the normal boiling point of the solvent. In various embodiments, the reaction temperature is at least 1, 2, 5, 10, 15, 20, 25, 30, 40, 50, 60, 70, 80, or 90 degrees Celsius below the normal boiling point of the solvent.

In some embodiments, the effective reaction conditions in step (d) include a reaction time from about 1 minute to about 120 hours. In various embodiments, the reaction time is about, at least about, or at most about 1, 5, 10, 30, or 60 minutes, or about 1, 2, 4, 8, 16, 24, 48, 96, or 120 hours, including any intervening ranges.

In some embodiments, the effective reaction conditions in step (d) include a reaction pH from about 0.5 to about 12. In various embodiments, the reaction pH is about, at least about, or at most about 0.5, 1, 2, 3, 4, 5, 6, 7, 8, 9, 10, 11, or 12, including any intervening ranges.

In some embodiments, the cannabinoid derivative is an isomer of the cannabinoid. In these embodiments, the effective reaction conditions may include the use of an isomerization catalyst. The isomerization catalyst may be an acid, a base, or an enzyme, for example.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. When the hydrogenation catalyst is disposed on a catalyst support, the catalyst support may be selected from the group consisting of activated carbon, alumina, silica, aluminosilicate, and combinations thereof.

When hydrogenation is employed, the hydrogenation may convert a cannabinoid into a hydrogenated cannabinoid. Alternatively, or additionally, the hydrogenation may convert a cannabinoid derivative into a hydrogenated cannabinoid derivative.

In certain embodiments, the cannabinoid derivative is selected from D8-THC, D8-THCa, D8-iso-THC, D9-THC, D9-THCa, or a combination thereof, and the hydrogenated cannabinoid derivative is HHC. That HHC may be a racemic mixture of 9R-HHC and 9S-HHC. A ratio of the 9R-HHC to the 9S-HHC may be controlled by selecting the hydrogenation catalyst, the effective reaction conditions, and/or a ratio of (D8-THC+D8-THCa+D8-iso-THC) to (D9-THC+D9-THCa). The ratio (D8-THC+D8-THCa+D8-iso-THC) to (D9-THC+D9-THCa) may be referred to as a D8-THC/D9-THC ratio.

In some embodiments, the process further comprises filtering and recycling the hydrogenation catalyst. The hydrogenation catalyst may be regenerated prior to recycling, if needed.

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt.

In some embodiments, the effective reaction conditions in step (d) include exposure to an acid catalyst. The acid catalyst may be an aprotic Lewis acid. In some embodiments, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is zinc bromide. In certain embodiments, the acid catalyst is an aluminosilicate, which may be in the form of molecular sieves.

In some embodiments, the conversion reactor is a packed-bed reactor. The packed-bed reactor may contain a packing material comprising an acid catalyst. The packed-bed reactor may contain a packing material comprising molecular sieves, whether or not the molecular sieves possess catalytic activity. The packed-bed reactor may contain a packing material comprising an acid catalyst as well as molecular sieves, wherein the acid catalyst and the molecular sieves are mixed together. The packed-bed reactor may contain a plurality of chambers, wherein at least a first chamber contains a first packing material comprising molecular sieves, and wherein at least a second chamber contains a second packing material comprising an acid catalyst. The second packing material may further comprise additional molecular sieves.

In some embodiments, step (e) includes exposing the reaction mixture to a flocculant. The flocculant may form a floc comprising the flocculant combined with a reaction byproduct, a solvent emulsion, an impurity, or a combination thereof. In certain embodiments, the flocculant pulls material from a non-polar layer.

In some embodiments, the flocculant is a polysaccharide, such as a polysaccharide selected from the group consisting of chitosan, starch, cellulose, hemicellulose, nanocellulose, polyglucan, glycogen, chitin, glucose oligomers, xylose oligomers, and combinations thereof.

Alkanes are susceptible to emulsions in water. In some embodiments, the solvent may periodically or continuously be cleaned with a flocculant to remove any emulsions that may have formed. This can be done preemptively whether or not it is known if emulsions are present and/or after emulsions are detected. Removing solvent emulsions leaves behind purified solvent for better process repeatability.

In some embodiments, step (e) includes conveying the reaction mixture to a crystallization unit to purify the cannabinoid derivative. The reaction mixture may be cooled within the crystallization unit from a first temperature to a second temperature that is lower than the first temperature, to precipitate unreacted cannabinoid out of the reaction mixture, thereby generating a mother liquor containing the cannabinoid derivative.

In some embodiments, step (e) includes distilling the reaction mixture to purify the cannabinoid derivative. Distillation may be beneficial to remove color bodies, for example.

In some embodiments, step (e) includes chromatographically purifying the cannabinoid derivative.

Generally, step (e) may utilize evaporation, distillation, filtration, chromatography, membrane separation, or a combination thereof.

In some embodiments, the process further comprises recovering the solvent. The solvent may be recovered via vacuum extraction. The solvent may be recycled back to step (b).

In some embodiments, the starting composition is obtained from an external source. In other embodiments, the starting composition is obtained from exposing a starting cannabinoid-containing plant material to a process solvent (e.g., supercritical $CO_2$, acetone, methanol, and/or ethanol). In some embodiments, the starting composition is obtained from a chemical reaction of a starting cannabinoid-containing plant material, prior to and separate from step (d).

The starting cannabinoid-containing plant material may be selected from *Cannabis sativa, Cannabis indica, Cannabis ruderalis, Echinacea purpurea, Echinacea angustifolia, Acmella oleracea, Helichrysum umbraculigerum,* or *Radula marginata*.

In various embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof, acetylated variants thereof, and combinations of the foregoing.

In some embodiments, the process is continuous or semi-continuous. In other embodiments, the process is a batch or semi-batch process.

Yet other variations provide a process of converting a cannabinoid into a purified cannabinoid derivative utilizing flocculation, the process comprising:

(a) providing a starting composition comprising a cannabinoid;

(b) providing a solvent comprising a $C_9$-$C_{11}$ non-aromatic hydrocarbon;

(c) introducing the starting composition and the solvent to a conversion reactor;

(d) operating the conversion reactor at effective reaction conditions to chemically convert the cannabinoid to a cannabinoid derivative at a cannabinoid conversion selected from about 10% to about 100%, thereby generating a reaction mixture;

(e) exposing the reaction mixture to a flocculant; and (f) isolating and recovering the cannabinoid derivative from the reaction mixture.

Figure 4:
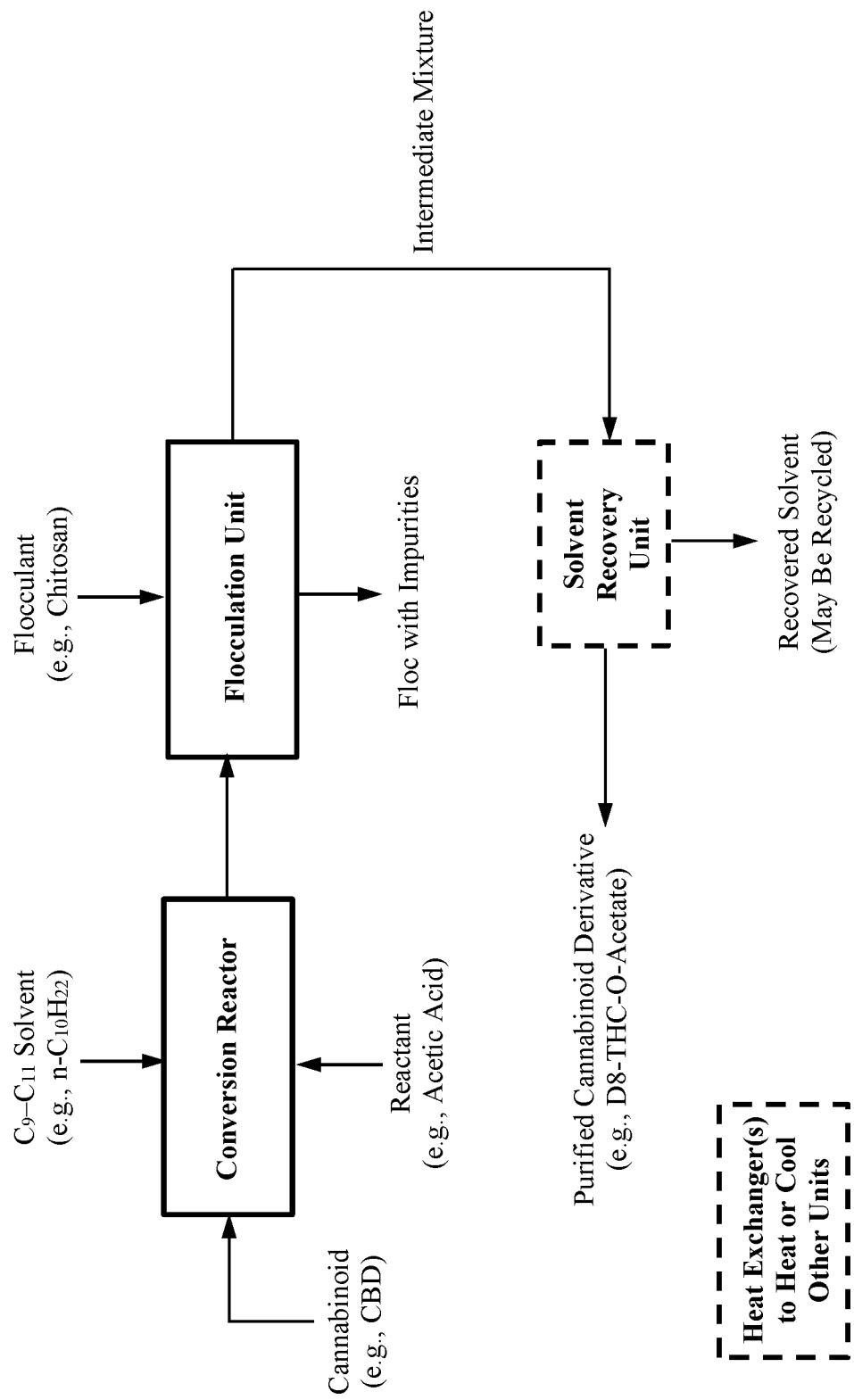
FIG. 4 is an exemplary block-flow diagram of a process and system for converting a cannabinoid into a purified cannabinoid derivative, in some embodiments.

FIG. 4 is an exemplary block-flow diagram of a process and system for converting a cannabinoid into a purified cannabinoid derivative, in some embodiments.

The cannabinoid may be selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the cannabinoid is cannabidiol, cannabigerol, or a mixture thereof.

In some embodiments, the starting composition is characterized by a cannabinoid purity of at least about 75 vol % or at least about 90 vol %, wherein the cannabinoid purity is calculated as mass of the cannabinoid divided by mass of all cannabinoids contained in the starting composition.

In some embodiments, during step (c), a cannabinoid/solvent ratio is selected from about 0.5 to about 2.0, calculated as volume of the cannabinoid divided by volume of the $C_9$-$C_{11}$ non-aromatic hydrocarbon solvent. In certain embodiments, the cannabinoid/solvent ratio is selected from about 0.8 to about 1.2.

In some embodiments, the $C_9$-$C_{11}$ non-aromatic hydrocarbon is a $C_{10}$ linear, cyclic, or branched alkane, alkene, or alkyne. The $C_9$-$C_{11}$ non-aromatic hydrocarbon may include, or consist essentially of, n-decane.

In some embodiments, the $C_9$-$C_{11}$ non-aromatic hydrocarbon is a $C_9$ linear, cyclic, or branched alkane, alkene, or alkyne.

In some embodiments, the $C_9$-$C_{11}$ non-aromatic hydrocarbon is a $C_{11}$ linear, cyclic, or branched alkane, alkene, or alkyne.

In some embodiments, the starting composition and the solvent are blended together and introduced to the conversion reactor.

In some embodiments, the effective reaction conditions include a reaction temperature selected from about 20° C. to about 170° C., such as from about 50° C. to about 170° C., or from about 100° C. to about 130° C. In certain embodiments, the reaction temperature is selected to be below the normal boiling point of the solvent.

In some embodiments, the effective reaction conditions in step (d) include a reaction time from about 1 minute to about 120 hours. In some embodiments, the effective reaction conditions in step (d) include a reaction pH from about 0.5 to about 12.

In some embodiments, the cannabinoid derivative is an isomer of the cannabinoid. Isomerization may be catalyzed or uncatalyzed.

In some embodiments, the effective reaction conditions include hydrogenation with hydrogen in the presence of a hydrogenation catalyst. The hydrogenation catalyst may be selected from the group consisting of platinum, palladium, rhodium, nickel, cobalt, ruthenium, iridium, and combination thereof, wherein the hydrogenation catalyst is optionally disposed on a catalyst support. The optional catalyst support may be selected from the group consisting of activated carbon, alumina, silica, aluminosilicate, and combinations thereof. The hydrogenation catalyst may be filtered and recycled, optionally with treatment (e.g., regeneration or reactivation) prior to recycling.

In some embodiments, hydrogenation converts a cannabinoid into a hydrogenated cannabinoid. In these or other embodiments, the hydrogenation may convert a cannabinoid derivative into a hydrogenated cannabinoid derivative. For example, a cannabinoid derivative selected from D8-THC, D8-THCa, D8-iso-THC, D9-THC, D9-THCa, or a combination thereof, may be hydrogenated into the hydrogenated cannabinoid derivative HHC. That HHC may be a racemic mixture of 9R-HHC and 9S-HHC. A ratio of the 9R-HHC to the 9S-HHC may be controlled by selecting the hydrogenation catalyst, the effective reaction conditions, and/or a ratio of (D8-THC+D8-THCa+D8-iso-THC) to (D9-THC+D9-THCa).

In some embodiments, the effective reaction conditions include acetylation of the cannabinoid with acetic acid or an acetate salt. In these or other embodiments, the effective reaction conditions may include acetylation of the cannabinoid derivative with acetic acid or an acetate salt.

In some embodiments, the effective reaction conditions in step (d) include exposure to an acid catalyst. The acid catalyst may be an aprotic Lewis acid. In some embodiments, the acid catalyst is selected from the group consisting of phosphoric acid, p-toluenesulfonic acid, citric acid, metal chlorides, metal bromides, metal fluorides, iodine-based acids, and combinations thereof. In certain embodiments, the acid catalyst is zinc bromide. In other embodiments, the acid catalyst is an aluminosilicate, which may be in the form of molecular sieves.

In some embodiments, the conversion reactor is a packed-bed reactor. The packed-bed reactor may contain a packing material comprising an acid catalyst. The packed-bed reactor may contain a packing material comprising molecular sieves. The packed-bed reactor may contain a packing material comprising an acid catalyst as well as molecular sieves, wherein the acid catalyst and the molecular sieves are mixed together. The packed-bed reactor may contain a plurality of chambers, wherein at least a first chamber contains a first packing material comprising molecular sieves, and wherein at least a second chamber contains a second packing material comprising an acid catalyst. The second packing material may further comprise additional molecular sieves.

In some embodiments, the flocculant forms a floc comprising the flocculant combined with a reaction byproduct, a solvent emulsion, an impurity, or a combination thereof. The flocculant may be a polysaccharide. The polysaccharide may be selected from the group consisting of chitosan, starch, cellulose, hemicellulose, nanocellulose, polyglucan, glycogen, chitin, glucose oligomers, xylose oligomers, and combinations thereof. In certain embodiments, the flocculant is chitosan.

In some embodiments, the process further comprises conveying the reaction mixture to a crystallization unit, in step (e) or step (f). The reaction mixture may be cooled within the crystallization unit from a first temperature to a second temperature that is lower than the first temperature, to precipitate unreacted cannabinoid out of the reaction mixture, thereby generating a mother liquor containing the cannabinoid derivative.

In some embodiments, step (f) includes distilling the reaction mixture to purify the cannabinoid derivative. In these or other embodiments, step (f) includes chromatographically purifying the cannabinoid derivative. In various embodiments, step (f) utilizes evaporation, distillation, filtration, chromatography, membrane separation, or a combination thereof.

In some embodiments, the process further comprises recovering the solvent. The solvent may be recovered via vacuum extraction. The recovered solvent may be recycled back to step (b).

In some embodiments, the starting composition is obtained from an external source. In other embodiments, the starting composition is obtained from exposing a starting cannabinoid-containing plant material to a process solvent (e.g., supercritical $CO_2$). The starting composition may be obtained from a chemical reaction of a starting cannabinoid-containing plant material, prior to and separate from step (d).

The starting cannabinoid-containing plant material may be selected from *Cannabis sativa, Cannabis indica, Cannabis ruderalis, Echinacea purpurea, Echinacea angustifolia, Acmella oleracea, Helichrysum umbraculigerum*, or *Radula marginata*.

In some embodiments, the cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof, acetylated variants thereof, and combinations of the foregoing.

In some embodiments, the process is continuous or semi-continuous. In other embodiments, the process is a batch or semi-batch process.

EXAMPLES

Example 1: CBD Isolation from CBD Distillate Using n-Decane

A starting CBD distillate is obtained with a CBD concentration of 75 wt %. The density of the CBD distillate is 950 kg/m$^3$.

The selected crystallization-inducing solvent is n-decane. The density of n-decane is 730 kg/m$^3$.

The basis is 1.333 L of CBD distillate. 1.333 L of CBD distillate is heated to 70° C. and mixed with 1 L of n-decane. 1.333 L of CBD distillate weighs 1,266 g. 1.333 L of CBD distillate contains 950 g of CBD. 1 L of n-decane weighs 730 g. The mass ratio of solvent to CBD is 0.77.

The mixture is allowed to passively or actively cool to room temperature, i.e. about 25° C. (for higher effectiveness, the mixture is cooled to about 0° C.). Once cooled to the reduced temperature, the CBD crystals are filtered out and the mother liquor is left behind. This mother liquor contains CBD and all the other cannabinoids that do not crystalize. The mother liquor is characterized as shown in the Appendix hereto (Certificate of Analysis ML-112820).

The mass of the mother liquor is the solvent weight plus the non-CBD portion of the distillate with unprecipitated CBD. With the basis above, this works out to 1,132.33 g.

To calculate the amount of CBD that did not precipitate, take 1,132.33 g and multiply it by the concentration of the mother liquor which is about 8.3 wt %. This calculation results in 93.5 g of CBD.

Finally, we can calculate the efficiency of this solvent as $$(1-(93.5 \text{ g}/950 \text{ g}))\times 100 = 90.2\%$$

Comparatively, pentane and n-heptane as crystallization-inducing solvents can only reach a maximum efficiency of 70%, but even to do so the mixture must be cooled severely down to −50° C. Commercially, it is uneconomical to bring down large mixtures to −50° C., which subsequently has a large impact on the bottom line. Surprisingly, it has been discovered that n-decane, as the crystallization-inducing solvent, can produce more efficient results at a much higher temperature compared to other hydrocarbon solvents (e.g., $C_5$-$C_7$ alkanes).

Example 2: Production of D9-THC from CBD

This example is predicated on the discovery of n-decane as a surprisingly effective solvent for inducing the precipitation of CBD, demonstrated in Example 1. The present inventor has realized that crystallization of CBD can be utilized to remove unreacted CBD in a conversion reaction to D9-THC, such that the D9-THC product becomes purified. By stopping the reaction before complete (or nearly complete) conversion of CBD to D9-THC, the generation of side products is inhibited, both from unreacted CBD (unselective chemistry) as well as from D9-THC (product decomposition or further conversion). Normally, stopping a reaction before completion results in the problem that the reactant needs to be separated from the product. However, crystallization of unreacted CBD results in very efficient separation and hence purification of the desired product, D9-THC. The unreacted CBD may be recycled for further conversion. It is emphasized that this Example 2 is directed to conversion of CBD to D9-THC, but other embodiments of the invention are applicable for conversion of other cannabinoids or terpenes to cannabinoid derivatives or terpene derivatives, respectively.

250 kg of CBD isolate, at least 99 wt % purity, is charged to a 1,000 liter tank. A programmable logic controller (PLC) measures the amount of CBD added and pumps n-decane into the tank at a 1:1 v/v ratio of n-decane to CBD. In prior experiments, a 1:1 v/v ratio has proved to increase mass transfer and kinetics of the desired reaction, as well as being advantageous for a high efficiency of the downstream crystallization of CBD.

The tank is heated to ensure that all the components are thoroughly homogeneous. The PLC then pumps the CBD/n-decane mixture through a first heat exchanger to further increase the temperature to the specified temperature, such as 80° C. The conversion may be conducted at a variety of temperatures and will generally only affect the reaction time.

After passing through the first heat exchanger, the CBD/n-decane mixture passes through a four-chambered packed-bed column. The first two chambers contain molecular sieves which are meant to absorb water from the mixture. Water is a catalyst poison. Also, water removal decrease formation of side products (e.g., from hydrolysis). The last two chambers contain a mixture of catalyst and molecular sieves. Molecular sieves are mixed with the catalyst to ensure that there is enough void space for low pressure drop across the column and to further keep water away from the catalyst. All materials utilized in the packed-bed column chambers are initially packed in 50-micron nylon bags to further aid in contamination prevention and operator safety.

Preferred catalysts are Lewis Acids that are aprotic. Aprotic Lewis catalysts help prevent the formation of D8-THC which is the thermodynamic product of the reaction of CBD. Also, most Lewis acids are generally insoluble in non-polar solvents and help prevent catalyst contamination in the product stream. Many different acids work in the conversion of CBD into D9-THC, including phosphoric acid, p-toluenesulfonic acid (P-TSA), citric acid, metal chlorides, metal bromides, metal fluorides, iodine-based acids, and others. It has previously been found that zinc bromide works well for useability, solubility, and efficiency of conversion.

Once the CBD/n-decane mixture has spent the operator-defined time of circulation through the tank, first heat exchanger, and packed bed, resulting in an intermediate mixture, the PLC then sends the intermediate mixture to a Nutsche crystallization unit. At the time of diversion, the preferred concentration of solution is about 40-60 wt % D9-THC and 60-40 wt % CBD. It is desired to prevent the reaction from progressing much beyond a 1:1 molar ratio, as the catalyst will begin to react with the D9-THC and convert it to undesired molecules. A Nutsche crystallizer is a preferred unit due to its ability to clean up and dry the resultant CBD crystals.

Once in the Nutsche unit, the intermediate mixture is pumped through a second heat exchanger to bring the intermediate mixture down to 0° C. The intermediate mixture is continuously pumped from the second heat exchanger to the Nutsche unit for an operator designated amounted of time, such as 1 hour. During the reduction in temperature, CBD will begin to precipitate from the solution. The precipitated CBD is filtered within the Nutsche unit by a 25-micron mesh screen located within the unit.

Due to the 90%+ efficiency of n-decane crystallizing CBD (per Example 1), the mother liquor produced from this step will contain the desired D9-THC. Based on the efficiency, the concentration of D9-THC is 90% or greater. The mother liquor may be referred to as the product mixture.

After the set amount of time, the mother liquor is pushed out and sent for solvent recovery utilizing compressed air. The CBD crystals may go through an optional washing step to ensure the greatest amount of D9-THC is removed. The CBD crystals are then heated and mixed under vacuum to ensure that all the solvent is fully recovered. The unreacted CBD may be utilized as starting material once again.

An optional chromatography step allows the product mixture to be further cleaned up to further remove CBD from the product mixture. This chromatography purification enables production of a pure D9-THC product. The product mixture may be sent to a product storage tank and ultimately may be sold, shipped, further treated, etc.

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A process of converting a cannabinoid into a purified cannabinoid derivative, said process comprising:
   (a) providing a starting composition comprising a cannabinoid;
   (b) providing a solvent comprising a C9-C11 non-aromatic hydrocarbon;
   (c) introducing said starting composition and said solvent to a conversion reactor;
   (d) operating said conversion reactor at effective reaction conditions to chemically convert said cannabinoid to a cannabinoid derivative at a cannabinoid conversion selected from about 10% to about 90%, thereby generating a reaction mixture containing unreacted cannabinoid;
   (e) conveying said reaction mixture to a crystallization unit;
   (f) within said crystallization unit, cooling said reaction mixture from a first temperature to a second temperature that is lower than said first temperature, to precipitate at least about 50% of said unreacted cannabinoid out of said reaction mixture, thereby generating a mother liquor containing said cannabinoid derivative; and
   (g) isolating and recovering said cannabinoid derivative from said mother liquor.

2. The process of claim 1, wherein said cannabinoid is selected from the group consisting of cannabidiol, cannabidiolic acid, cannabigerol, cannabigerolic acid, cannabinol, cannabichromene, cannabichromenic acid, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

3. The process of claim 1, wherein said cannabinoid is cannabidiol.

4. The process of claim 1, wherein said cannabinoid is cannabigerol.

5. The process of claim 1, wherein said starting composition is characterized by a cannabinoid purity of at least about 90 vol %, wherein said cannabinoid purity is calculated as mass of said cannabinoid divided by mass of all cannabinoids contained in said starting composition.

6. The process of claim 1, wherein during step (c), a cannabinoid/solvent ratio is selected from about 0.5 to about 2.0, calculated as volume of said cannabinoid divided by volume of said C9-C11 non-aromatic hydrocarbon solvent.

7. The process of claim 6, wherein said cannabinoid/solvent ratio is selected from about 0.8 to about 1.2.

8. The process of claim 1, wherein said C9-C11 non-aromatic hydrocarbon is a C10 linear, cyclic, or branched alkane, alkene, or alkyne.

9. The process of claim 1, wherein said C9-C11 non-aromatic hydrocarbon includes n-decane.

10. The process of claim 1, wherein said C9-C11 non-aromatic hydrocarbon is a C9 linear, cyclic, or branched alkane, alkene, or alkyne.

11. The process of claim 1, wherein said C9-C11 non-aromatic hydrocarbon is a C11 linear, cyclic, or branched alkane, alkene, or alkyne.

12. The process of claim 1, wherein said starting composition and said solvent are blended together and introduced to said conversion reactor.

13. The process of claim 1, wherein said cannabinoid conversion is selected from about 20% to about 80%.

14. The process of claim 1, wherein said cannabinoid conversion is selected from about 30% to about 70%.

15. The process of claim 1, wherein said effective reaction conditions in step (d) include a reaction temperature from about −20° C. to about 200° C.

16. The process of claim 1, wherein said effective reaction conditions in step (d) include a reaction time from about 1 minute to about 120 hours.

17. The process of claim 1, wherein said effective reaction conditions in step (d) include a reaction pH from about 0.5 to about 12.

18. The process of claim 1, wherein said cannabinoid derivative is an isomer of said cannabinoid.

19. The process of claim 1, wherein said effective reaction conditions include hydrogenation with hydrogen in the presence of a hydrogenation catalyst.

20. The process of claim 19, wherein said hydrogenation catalyst is selected from the group consisting of platinum, palladium, rhodium, nickel, cobalt, ruthenium, iridium, and combination thereof, wherein said hydrogenation catalyst is optionally disposed on a catalyst support.

21. The process of claim 20, wherein said hydrogenation catalyst is disposed on said catalyst support, and wherein said catalyst support is selected from the group consisting of activated carbon, alumina, silica, aluminosilicate, and combinations thereof.

22. The process of claim 19, wherein said hydrogenation converts a cannabinoid into a hydrogenated cannabinoid.

23. The process of claim 19, wherein said hydrogenation converts a cannabinoid derivative into a hydrogenated cannabinoid derivative.

24. The process of claim 23, wherein said cannabinoid derivative is selected from D8-THC, D8-THCa, D8-iso-THC, D9-THC, D9-THCa, or a combination thereof, and wherein said hydrogenated cannabinoid derivative is HHC.

25. The process of claim 24, wherein said HHC is a racemic mixture of 9R-HHC and 9S-HHC, and wherein a ratio of said 9R-HHC to said 9S-HHC is controlled by selecting said hydrogenation catalyst, said effective reaction conditions, and/or a ratio of (D8-THC+D8-THCa+D8-iso-THC) to (D9-THC+D9-THCa).

26. The process of claim 19, further comprising filtering and recycling said hydrogenation catalyst.

27. The process of claim 1, wherein said effective reaction conditions include acetylation of said cannabinoid with acetic acid or an acetate salt.

28. The process of claim 1, wherein said effective reaction conditions include acetylation of said cannabinoid derivative with acetic acid or an acetate salt.

29. The process of claim 1, wherein said effective reaction conditions in step (d) include exposure to an acid catalyst.

30. The process of claim 29, wherein said acid catalyst is an aprotic Lewis acid.

31. The process of claim 29, wherein said acid catalyst is selected from the group consisting of phosphoric acid, p-toluenesulfonic acid, citric acid, metal chlorides, metal bromides, metal fluorides, iodine-based acids, and combinations thereof.

32. The process of claim 29, wherein said acid catalyst is zinc bromide.

33. The process of claim 29, wherein said acid catalyst is an aluminosilicate.

34. The process of claim 33, wherein said aluminosilicate is in the form of a molecular sieve.

35. The process of claim 1 wherein said conversion reactor is a packed-bed reactor.

36. The process of claim 35, wherein said packed-bed reactor contains a packing material comprising an acid catalyst.

37. The process of claim 35, wherein said packed-bed reactor contains a packing material comprising molecular sieves.

38. The process of claim 35, wherein said packed-bed reactor contains a packing material comprising an acid catalyst as well as molecular sieves, wherein said acid catalyst and said molecular sieves are mixed together.

39. The process of claim 35, wherein said packed-bed reactor contains a plurality of chambers, wherein at least a first chamber contains a first packing material comprising molecular sieves, and wherein at least a second chamber contains a second packing material comprising an acid catalyst.

40. The process of claim 39, wherein said second packing material further comprises additional molecular sieves.

41. The process of claim 1, wherein said crystallization unit is a Nutsche unit.

42. The process of claim 1, wherein said first temperature is selected from about 20° C. to about 170° C.

43. The process of claim 1, wherein said first temperature is selected from about 30° C. to about 100° C.

44. The process of claim 1, wherein said second temperature is selected from about −20° C. to about 150° C.

45. The process of claim 1, wherein said second temperature is selected from about −10° C. to about 100° C.

46. The process of claim 1, wherein said second temperature is selected from about 0° C. to about 50° C.

47. The process of claim 1, wherein the temperature difference between said first temperature and said second temperature is from about 10° C. to about 200° C.

48. The process of claim 47, wherein said temperature difference is from about 20° C. to about 100° C.

49. The process of claim 1, wherein at least about 75% of said unreacted cannabinoid is precipitated out of said reaction mixture.

50. The process of claim 1, wherein at least about 90% of said unreacted cannabinoid is precipitated out of said reaction mixture.

51. The process of claim 1, wherein step (g) comprises separating said cannabinoid derivative from said mother liquor by utilizing a compressed gas.

52. The process of claim 1, wherein said process further comprises recovering said solvent.

53. The process of claim 52, wherein said solvent is recovered via vacuum extraction.

54. The process of claim 52, wherein said solvent is recycled back to step (b).

55. The process of claim 1, wherein said unreacted cannabinoid that is precipitated in step (f) is washed to remove residual cannabinoid derivative.

56. The process of claim 1, wherein said unreacted cannabinoid that is precipitated in step (f) is reused in step (a) as at least a portion of said starting composition.

57. The process of claim 56, wherein said crystallization unit is a Nutsche unit, and wherein said unreacted cannabinoid that is precipitated in step (f) is recovered using a mesh screen disposed within said Nutsche unit.

58. The process of claim 1, wherein step (g) utilizes evaporation, distillation, filtration, chromatography, membrane separation, or a combination thereof.

59. The process of claim 1, wherein said process further comprises chromatographic purification of said cannabinoid derivative between step (f) and step (g), as part of step (g), or following step (g).

60. The process of claim 1, wherein said starting composition is obtained from an external source.

61. The process of claim 1, wherein said starting composition is obtained from exposing a starting cannabinoid-containing plant material to a process solvent.

62. The process of claim 61, wherein said process solvent is supercritical carbon dioxide.

63. The process of claim 61, wherein said process solvent is not a C9-C11 non-aromatic hydrocarbon.

64. The process of claim 1, wherein said starting composition is obtained from a chemical reaction of a starting cannabinoid-containing plant material, prior to and separate from step (d).

65. The process of claim 64, wherein said starting cannabinoid-containing plant material is selected from *Cannabis sativa, Cannabis indica, Cannabis ruderalis, Echinacea purpurea, Echinacea angustifolia, Acmella oleracea, Helichrysum umbraculigerum*, or *Radula marginata*.

66. The process of claim 1, wherein said cannabinoid derivative is selected from the group consisting of CBD, CBDa, CBG, CBGa, D6-THC, D6-THCa, D8-THC, D8-THCa, D8-iso-THC, D9-THC, D9-THCa, D10-THC, D10-THCa, Exo-THC, Exo-THCa, CBN, CBNa, CBT (Tran), CBTa (Tran), CBT (Triol), CBTa (Triol), CBC, CBCa, CBL, CBLa, CBDV, CBDva, D6-THCV, D6-THCVa, D8-THCV, D8-THCVa, D9-THCV, D9-THCVa, D10-THCV, D10-THCVa, Exo-THCV, Exo-THCVa, CBGV, CBGVa, CBNV, CBNVa, CBTv (Tran), CBTva (Tran), CBTv (Triol), CBTva (Triol), CBCv, CBCva, CBLv, CBLva, CBDp, CBDpa, D6-THCp, D6-THCpa, D8-THCp, D8-THCpa, D9-THCp, D9-THCpa, D10-THCp, D10-THCpa, Exo-THCp, Exo-THCpa, CBGp, CBGpa, CBNp, CBNpa, CBTp (Tran), CBTpa (Tran), CBTp (Triol), CBTpa (Triol), CBCp, CBCpa, CBLp, CBLpa, CBDo, CBDoa, D6-THCo, D6-THCoa, D8-THCo, D8-THCoa, D9-THCo, D9-THCoa, D10-THCo, D10-THCoa, Exo-THCo, Exo-THCoa, CBGo, CBGoa, CBNo, CBNoa, CBTo (Tran), CBToa (Tran), CBTo (Triol), CBToa (Triol), CBCo, CBCoa, CBLo, CBLoa, CBDb, CBDba, D6-THCb, D6-THCba, D8-THCb, D8-THCba, D9-THCb, D9-THCba, D10-THCb, D10-THCba, Exo-THCb, Exo-THCba, CBGb, CBGba, CBNb, CBNba, CBTb (Tran), CBTba (Tran), CBTb (Triol), CBTba (Triol), CBCb, CBCba, CBLb, CBLba, hydrogenated variants thereof, acetylated variants thereof, and combinations of the foregoing.

67. The process of claim 1, wherein said cannabinoid derivative includes D9-THC.

68. The process of claim 1, wherein said cannabinoid derivative includes HHC.

69. The process of claim 1, wherein said process is continuous or semi-continuous.

70. A system for converting a cannabinoid into a purified cannabinoid derivative, said system comprising:
a conversion reactor configured with at least one inlet for a starting composition comprising a cannabinoid as well as a solvent comprising a C9-C11 non-aromatic hydrocarbon, wherein said conversion reactor is configured to chemically convert some, but not all, of said cannabinoid to a cannabinoid derivative at a cannabinoid conversion, thereby generating a reaction mixture containing unreacted cannabinoid;
a crystallization unit in flow communication with said conversion reactor, wherein said crystallization unit is configured to cool said reaction mixture to precipitate unreacted cannabinoid out of said reaction mixture, thereby generating a mother liquor containing said cannabinoid derivative;
a solvent recovery unit in flow communication with said crystallization unit, where-in said solvent recovery unit is configured to remove said solvent from said mother liquor to generate a purified cannabinoid derivative; and
one or more heat exchangers configured to heat and/or cool said conversion reactor, said crystallization unit, and/or said solvent recovery unit.

71. The system of claim 70, wherein said C9-C11 non-aromatic hydrocarbon is a C10 linear, cyclic, or branched alkane, alkene, or alkyne.

72. The system of claim 70, wherein said C9-C11 non-aromatic hydrocarbon includes n-decane.

73. The system of claim 70, wherein said C9-C11 non-aromatic hydrocarbon consists essentially of n-decane.

74. The system of claim 70, wherein said C9-C11 non-aromatic hydrocarbon is a C9 linear, cyclic, or branched alkane, alkene, or alkyne.

75. The system of claim 70, wherein said C9-C11 non-aromatic hydrocarbon is a C11 linear, cyclic, or branched alkane, alkene, or alkyne.

76. The system of claim 70, wherein said conversion reactor is a packed-bed reactor.

77. The system of claim 76, wherein said packed-bed reactor contains a packing material comprising an acid catalyst.

78. The system of claim 77, wherein said acid catalyst is an aprotic Lewis acid.

79. The system of claim 77, wherein said acid catalyst is selected from the group consisting of phosphoric acid, p-toluenesulfonic acid, citric acid, metal chlorides, metal bromides, metal fluorides, iodine-based acids, and combinations thereof.

80. The system of claim 77, wherein said acid catalyst is zinc bromide.

81. The system of claim 77, wherein said acid catalyst is an aluminosilicate.

82. The system of claim 76, wherein said packed-bed reactor contains a packing material comprising molecular sieves.

83. The system of claim 76, wherein said packed-bed reactor contains a packing material comprising an acid catalyst as well as molecular sieves, wherein said acid catalyst and said molecular sieves are mixed together.

84. The system of claim 76, wherein said packed-bed reactor contains a plurality of chambers, wherein at least a first chamber contains a first packing material comprising molecular sieves, and wherein at least a second chamber contains a second packing material comprising an acid catalyst.

85. The system of claim 84, wherein said second packing material further comprises additional molecular sieves.

86. The system of claim 70, wherein said crystallization unit is a Nutsche unit.

87. The system of claim 86, wherein said Nutsche unit includes a mesh screen configured for recovering precipitated, unreacted cannabinoid.

88. The system of claim 70, wherein said solvent recovery unit is configured to recover said solvent using a compressed gas.

89. The system of claim 70, wherein said solvent recovery unit is a vacuum extraction unit.

90. The system of claim 70, wherein said system further comprises a chromatographic purification unit configured to purify said cannabinoid derivative.

91. The system of claim 90, wherein said chromatographic purification unit is disposed between said crystallization unit and said solvent recovery unit.

92. The system of claim 90, wherein said chromatographic purification unit is disposed between said solvent recovery unit and a product storage tank or container.

93. The system of claim 70, wherein said system is configured to operate continuously or semi-continuously.

94. The system of claim 70, wherein said system is automated using a programmable logic controller.

* * * * *